United States Patent
Palczewski et al.

(10) Patent No.: US 10,272,106 B2
(45) Date of Patent: Apr. 30, 2019

(54) COMPOSITIONS AND METHODS OF TREATING DIABETIC RETINOPATHY

(71) Applicant: CASE WESTERN RESERVE UNIVERSITY, Cleveland, OH (US)

(72) Inventors: Krzysztof Palczewski, Cleveland, OH (US); Timothy Kern, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/316,412

(22) PCT Filed: Jun. 4, 2015

(86) PCT No.: PCT/US2015/034189
§ 371 (c)(1),
(2) Date: Dec. 5, 2016

(87) PCT Pub. No.: WO2015/187942
PCT Pub. Date: Dec. 10, 2015

(65) Prior Publication Data
US 2017/0196908 A1    Jul. 13, 2017

Related U.S. Application Data

(60) Provisional application No. 62/007,710, filed on Jun. 4, 2014.

(51) Int. Cl.
A61K 33/24    (2006.01)
A61K 31/352    (2006.01)
(Continued)

(52) U.S. Cl.
CPC ............ *A61K 33/24* (2013.01); *A61K 9/0048* (2013.01); *A61K 31/12* (2013.01); *A61K 31/13* (2013.01); *A61K 31/155* (2013.01); *A61K 31/197* (2013.01); *A61K 31/352* (2013.01); *A61K 31/4164* (2013.01); *A61K 31/4453* (2013.01); *A61K 31/48* (2013.01); *A61K 31/498* (2013.01);
(Continued)

(58) Field of Classification Search
None
See application file for complete search history.

(56) References Cited

U.S. PATENT DOCUMENTS

2009/0197967 A1    8/2009    Kubota et al.

FOREIGN PATENT DOCUMENTS

WO    WO 2008/147528 A1 *    12/2008    ............ G01N 33/53
WO    2013063269 A2    5/2013

OTHER PUBLICATIONS

Maeda, et al., "Primary amines protect against retinal degeneration in mouse models of retinopathies", Nature Chemical Biology, vol. 8, pp. 170-178, (2012).

(Continued)

*Primary Examiner* — Brian J Davis
(74) *Attorney, Agent, or Firm* — Tarolli, Sundheim, Covell & Tummino LLP

(57) ABSTRACT

A method of treating diabetic retinopathy in a subject in need thereof includes administering to the subject a therapeutically effective amount of one or more agents that act as a trap of reactive aldehydes and/or inhibit diabetes-induced superoxide generation and capillary degeneration regulated by GPCR signaling pathways.

14 Claims, 13 Drawing Sheets

(51) Int. Cl.
| | |
|---|---|
| *A61K 31/553* | (2006.01) |
| *A61K 31/58* | (2006.01) |
| *A61K 31/69* | (2006.01) |
| *A61K 31/7076* | (2006.01) |
| *A61K 9/00* | (2006.01) |
| *A61K 31/12* | (2006.01) |
| *A61K 31/155* | (2006.01) |
| *A61K 31/52* | (2006.01) |
| *A61K 31/4164* | (2006.01) |
| *A61K 31/498* | (2006.01) |
| *A61K 45/06* | (2006.01) |
| *A61K 31/197* | (2006.01) |
| *A61K 31/4453* | (2006.01) |
| *A61K 31/48* | (2006.01) |
| *A61K 31/505* | (2006.01) |
| *A61K 31/517* | (2006.01) |
| *A61K 31/13* | (2006.01) |

(52) U.S. Cl.
CPC .......... *A61K 31/505* (2013.01); *A61K 31/517* (2013.01); *A61K 31/52* (2013.01); *A61K 31/553* (2013.01); *A61K 31/58* (2013.01); *A61K 31/69* (2013.01); *A61K 31/7076* (2013.01); *A61K 45/06* (2013.01)

(56) References Cited

OTHER PUBLICATIONS

Du, et al., "Contribution of GPCRs and NADPH oxidase to increased generation of superoxide by retinal photorecepto cells in elevated glucose", Investigative Ophthalmology & Visual Science Jun. 2013, vol. 54, (ARVO Annual Meeting Abstract).
Extended European Search Report for Application No. 15802805.5-1109/3151818.
Supplementary European Search Report for Application No. 15802805.5-1109/3151818.

* cited by examiner

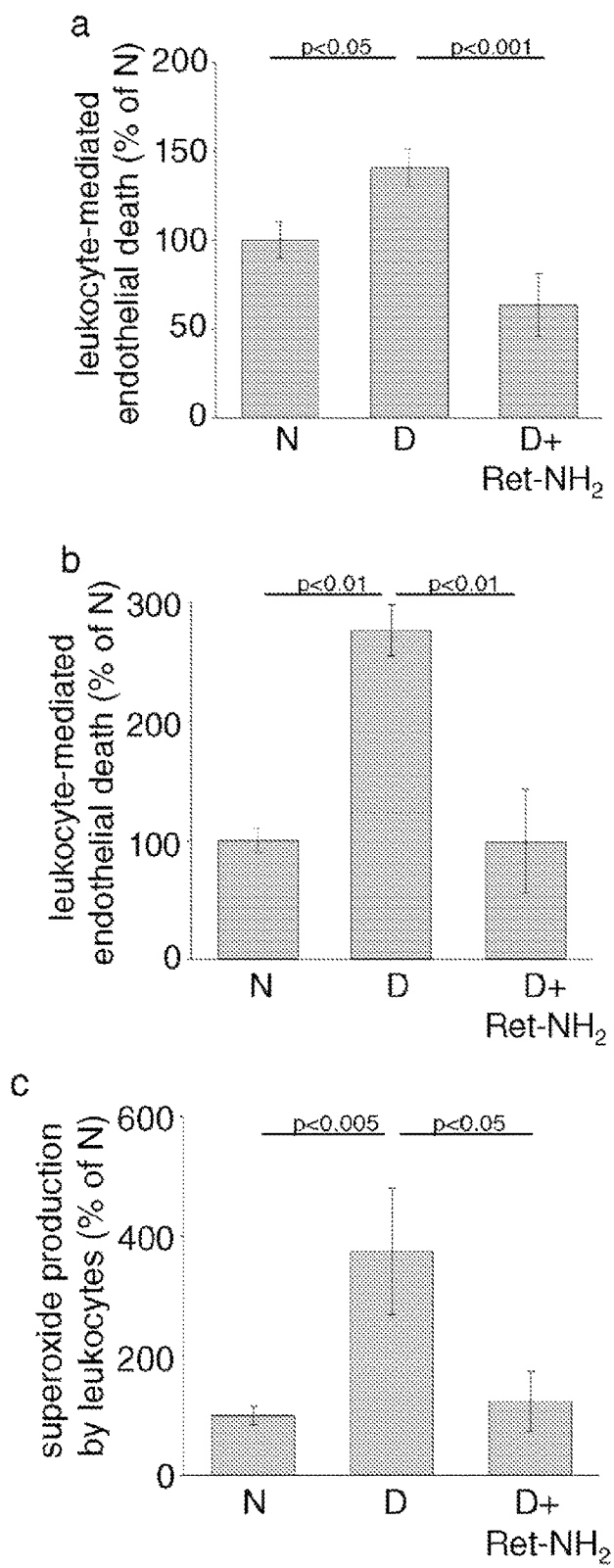
Figs. 6A-C

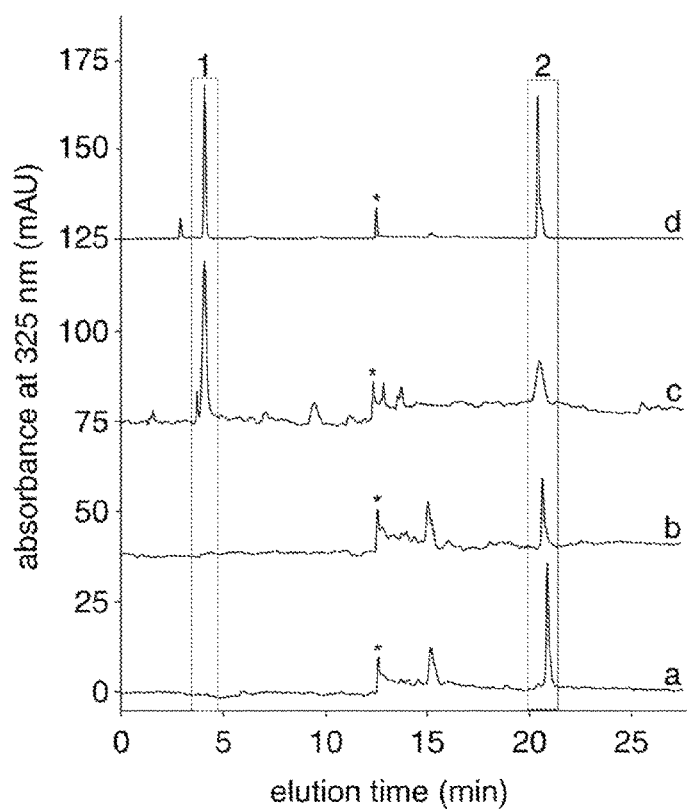
Fig. 7A-D
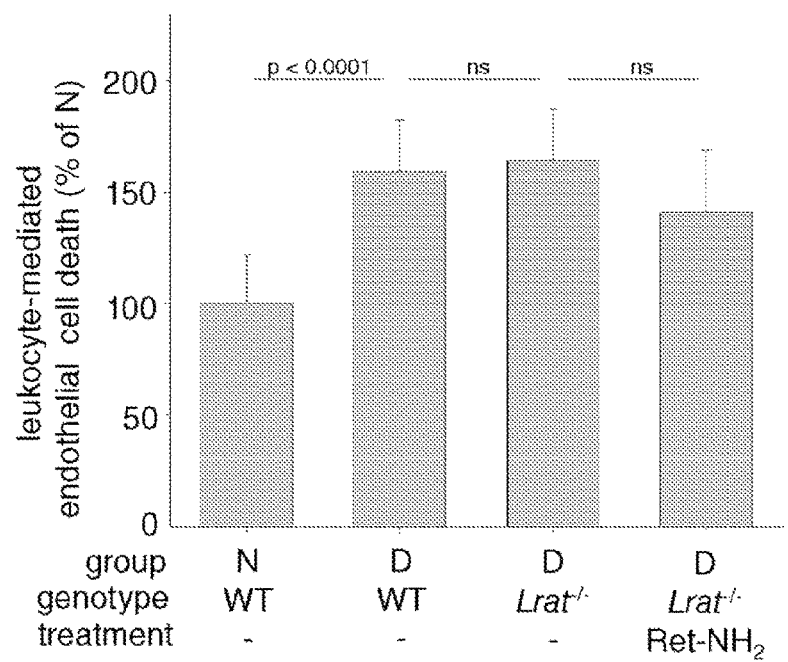
Fig. 8

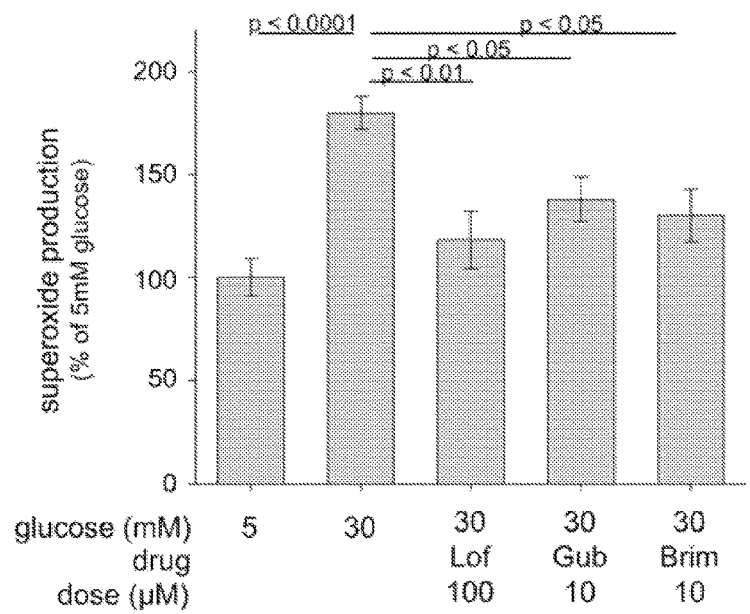
Fig. 15
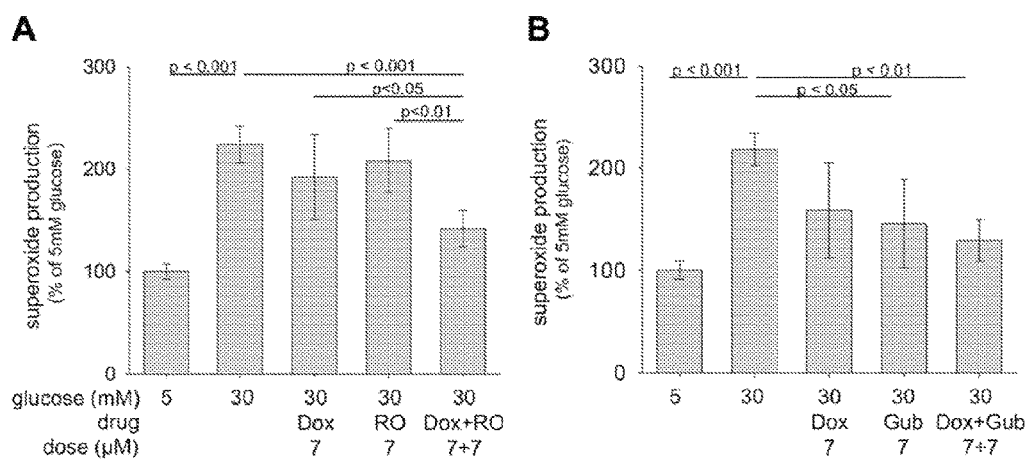
Figs. 16A-B

Figs. 19A-D

COMPOSITIONS AND METHODS OF TREATING DIABETIC RETINOPATHY

RELATED APPLICATION

This application claims priority from U.S. Provisional Application No. 62/007,710, filed Jun. 4, 2014, the subject matter of which is incorporated herein by reference in its entirety.

GOVERNMENT FUNDING

This invention was made with government support under Grant No. R01EY000300, R01EY022938, and R24EY021126 awarded by The National Institutes of Health. The United States government has certain rights to the invention.

BACKGROUND

Diabetic retinopathy (DR) has classically been regarded as a disease of the retinal microvasculature, and the natural history of the disease has been divided into an early, nonproliferative (or background) stage, and a later proliferative stage. These vascular lesions are largely responsible for the visual impairment/loss in advanced DR, and have been the focus of clinical trials to date. Though visual dysfunction and loss are less specific for diabetes, approval for therapies against DR from the FDA is based on therapies inhibiting these parameters in diabetic patients.

Vascular lesions in the early stages of DR in patients and animals are characterized histologically by the presence of obliterated and degenerated capillaries and pericyte-deficient capillaries. Capillary non-perfusion and degeneration are generally thought to play major roles in the progression to pre-retinal neovascularization that develops in some diabetic patients. As more capillaries become non-perfused or occluded, local areas of the retina likely become deprived of oxygen and nutrients, thus stimulating the production of one or more ischemia-driven growth factors (such as vascular endothelial growth factor (VEGF)) and the subsequent neovascular response. Progressive growth of abnormal vessels into the vitreous in proliferative DR (PDR) can lead to vitreous hemorrhage, pre-retinal hemorrhage, and eventually even to retinal detachment. Anti-VEGF therapies appear to inhibit or even reverse retinal neovascularization, with additional studies ongoing.

Increased vascular permeability is another alteration that leads to visual impairment in patients. Retinal edema seems to arise primarily from well-defined microaneurysms, but animal studies suggest that the leakage is more wide-spread. The pathophysiology of the edema apparently involves dilated capillaries, retinal microaneurysms, and impairment of the blood-retinal barrier, resulting in leakage of fluid into the extracellular space, thus disrupting macular structure and function. Diabetic macular edema (DME), defined as retinal edema involving or threatening the macula, is the most common cause of visual loss in DR. Whether the permeability defect is the only factor causing retinal edema in diabetes is unclear. Laser photocoagulation, anti-VEGF therapies, and steroids all can inhibit retinal edema in diabetes, although pharmacological approaches act only temporarily, and in about half of patients with DME.

Diabetes also results in dysfunction and degeneration of retinal neural cells. Loss of ganglion cells has been detected in diabetic rats and humans, but results in mice are controversial. Retinal electrophysiological abnormalities in diabetes include changes in ERGs, visual evoked potentials (VEPs), and subnormal oscillatory potential amplitudes. Recent clinical studies showed that inner and outer retinal function were impaired even during early (nonproliferative) stages of DR. Diabetes also impairs visual psychophysics, as evidenced by reductions in visual acuity, contrast sensitivity and color vision.

SUMMARY

Embodiments described herein relate to compounds and methods of treating diabetic retinopathy in a subject in need thereof. The methods can include administering to the subject a therapeutically effective amount of one or more agents that can act as traps of reactive aldehydes, inhibit degeneration of photoreceptors, and/or inhibit diabetes-induced superoxide generation and capillary degeneration regulated by GPCR signaling pathways. In some embodiments, the one or more agents that can act as traps of reactive aldehydes, inhibit degeneration of photoreceptors, and/or inhibit diabetes-induced superoxide generation and capillary degeneration regulated by GPCR signaling pathways can include primary amines that can act as a trap of reactive aldehyde in the retina, retinylamines, retinylamine derivatives, retinoid derivatives, agents that inhibit and/or antagonize the Gq signaling cascade (e.g., agents that inhibit or antagonize Gq-protein coupled receptor activation, alpha 1 adrenergic receptor ($\alpha_1$-AR) activation, PLC activation, $IP_3$ binding to its receptor, Ca+ accumulation in mitochondria, and NADPH oxidase activation), agents that inhibit or antagonize the Gs signaling cascade (e.g., agents that inhibit and/or antagonize Gs-protein coupled receptor activation, $5\text{-}HT_{2a}$ receptor activation, $5\text{-}HT_{2b}$ receptor activation, $5\text{-}HT_{2c}$ receptor activation, $5\text{-}HT_{2a/c}$ receptor activation, $5\text{-}HT_4$ receptor activation, $5\text{-}HT_6$ receptor activation, and $5\text{-}HT_7$ receptor activation, and adenylyl cyclase activation) and/or agents that activate Gi signaling cascade in a retina cell (e.g., Gi-protein coupled receptor agonists, alpha-2 adrenergic receptor agonists, and PKA activators). These agents can be used alone and/or in combination with each other at subtherapeutic doses as well as with other agents to treat diabetic retinopathy.

In some embodiments, the one or more agents can include at least one, two, three, or four or more of a primary amine that can act as a trap of reactive aldehyde in the retina, retinylamine, retinylamine derivatives, retinoid derivatives, an alpha 1 adrenergic receptor ($\alpha_1$-AR) antagonist, a PLC inhibitor, an $IP_3$ receptor inhibitor, an inhibitor of Ca+ accumulation in mitochondria, a NADPH oxidase inhibitor, a $5\text{-}HT_{2a}$ receptor antagonist, a $5\text{-}HT_{2b}$ receptor antagonist, a $5\text{-}HT_{2c}$ receptor antagonist, a $5\text{-}HT_{2a/c}$ receptor antagonist, a $5\text{-}HT_4$ receptor antagonist, a $5\text{-}HT_6$ receptor antagonist, $5\text{-}HT_7$ receptor antagonist, andenylyl cyclase inhibitor, an M3 receptor antagonist, an alpha-2 adrenergic receptor agonist, or a PKA activator.

In another embodiment, the agent(s) can be delivered to the subject by at least one of topical administration, systemic administration, and/or intraocular delivery including intravitreal injection. In one example, the agent(s) can be provided in an ocular preparation for sustained delivery. In another example, the agent(s) can be administered to the subject by parenteral and/or enteral administration.

BRIEF DESCRIPTION OF THE DRAWINGS

FIGS. 6(A-C) illustrate graphs showing leukocytes isolated from mice diabetic for (A) 2 months or (B) 8 months caused more cytotoxicity to retinal endothelial cells, and produced more superoxide than did leukocytes from age-matched non-diabetic mice (c; 8 months diabetes). In vivo treatment with Ret-NH$_2$ from the onset of diabetes suppressed all of these abnormalities. n=3-5 in all groups.

FIG. 7 illustrates plots showing lack of LRAT enzymatic activity in leukocytes or retinal endothelial cells prevents all-trans ester formation. Analysis of the retinoid composition extracted after incubation of all-trans-retinol with the leukocyte or retinal endothelial cell extracts (chromatograms "a" and "b", respectively) did not reveal presence of all-trans-retinyl esters, which were readily detectable in a sample extracted from bovine RPE microsomes, a positive control (chromatogram "c"). Peak 1 was identified as all-trans-retinyl palmitate based on its elution time and UV/Vis spectrum that was identical with a synthetic standard (chromatogram "d"). Peak 2 represents the substrate, all-trans-retinol.

FIG. 8 illustrates a graph showing blood leukocytes from Lrat−/− mice cause cytotoxicity to retinal endothelial cells comparable to that seen with leukocytes from WT diabetic mice. Ret-NH$_2$ only has only a partial effect to inhibit the cytotoxicity. n=5 in all groups.

FIG. 15 illustrates a graph showing the pharmacologic activation of a2-ARs (Gi pathway) inhibited the glucose-induced increase in superoxide generation by 661W cells. Lof, lofexidine; Gub, guanabenz; Brim, brimonidine.

FIGS. 16(A-B) illustrate graphs showing combinations of suboptimal doses of compounds that act on different G protein signaling pathways show additive effects on superoxide inhibition in 661W cells. Simultaneous inhibition of the Gq and Gs pathways with Dox and RO (RO-04-6790) or inhibition of the Gi and activation of the Gq pathways with Dox and Gub resulted in greater suppression of superoxide generation than single therapies.

DETAILED DESCRIPTION

Figure 1:
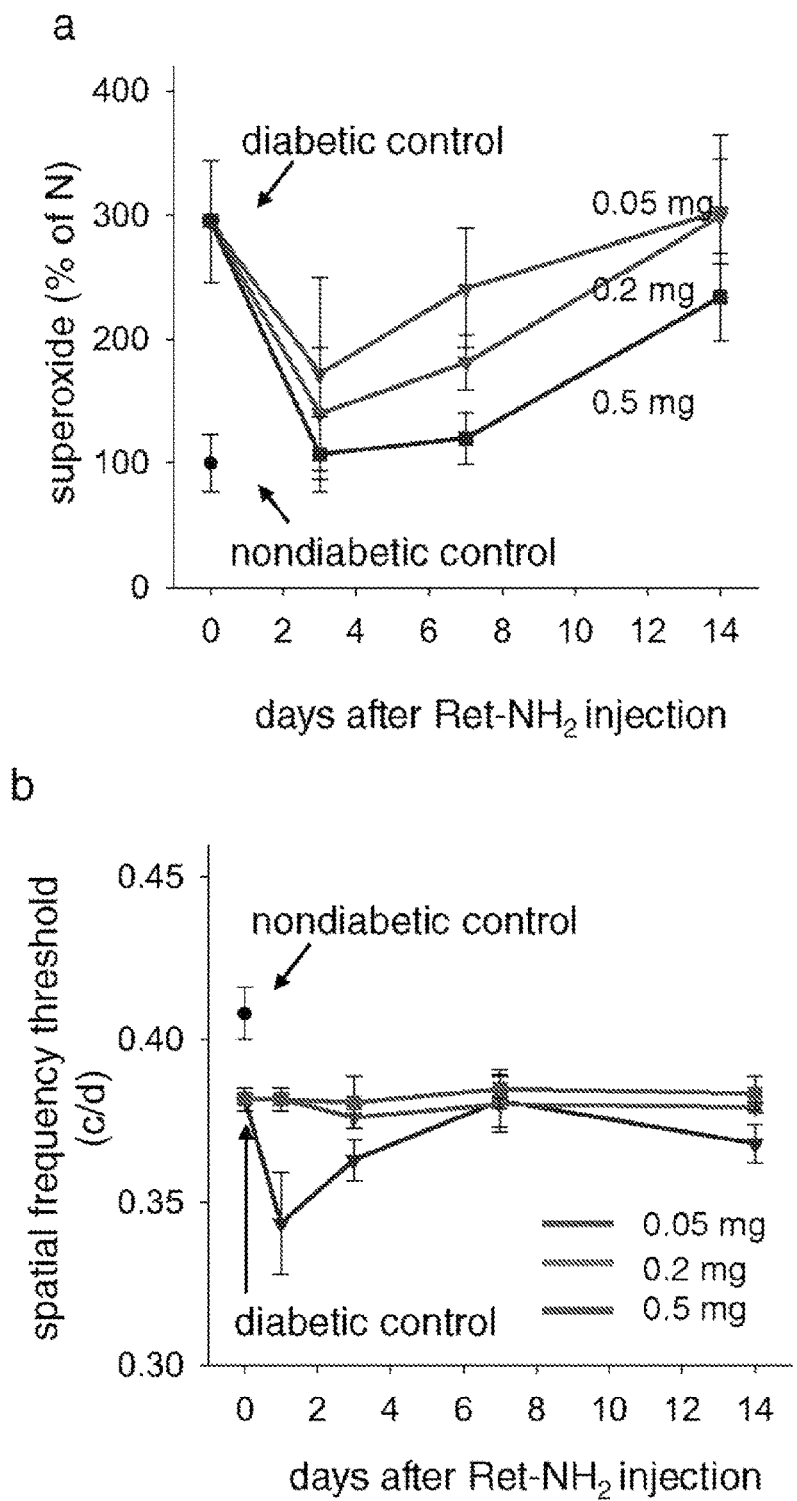
FIGS. 1(A-B) illustrate plots showing the effects of a single dose of Ret-NH$_2$ on retinal superoxide production and visual function in mice diabetic for 2 months (4 months of age). Retinal superoxide generation and spatial frequency threshold were measured 1, 3, 7 and 14 days after a single injection of Ret-NH$_2$. Superoxide was measured by the lucigenin method, and spatial frequency threshold was measured via the optokinetic method. n=5-9 in all groups.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refer to the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative", refers to compounds that have a common core structure, and are substituted with various groups as described herein. For example, all of the compounds represented by formula I are primary amines and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" refer to modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" refers to inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" refers to stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term a "pharmaceutical composition" refers to a formulation containing the disclosed compounds in a form suitable for administration to a subject. The pharmaceutical composition can be in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intraocular, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" refers to a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claims.

The phrase "pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present application is intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulfadryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like (e.g., Bundegaard, H. "Design of Prodrugs" p 1-92, Elesevier, New York-Oxford (1985)).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, $2^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" refers to a functional group that converts an amine, amide, or other nitrogen-containing moiety into a different chemical group that is substantially inert to the conditions of a particular chemical reaction. Amine protecting groups can be removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other amine protecting groups can be identified by those of skill in the art.

Representative hydroxy protecting groups include those where the hydroxy group is either acylated or alkylated, such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as primates, mammals, and vertebrates.

The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" refer to molecules and other agents that are biologically, physiologically, or pharmacologically active substances that act locally or systemically in a patient or subject to treat a disease or condition, such as diabetic retinopathy. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" refer to the dose of a drug, which produces 50% of its maximum response or effect, or alternatively, the dose, which produces a pre-determined response in 50% of test subjects or preparations. The term "LD50" refers to the dose of a drug, which is lethal in 50% of test subjects. The term "therapeutic index" refers to the therapeutic index of a drug, defined as LD50/ED50.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

As used herein, "halo" or "halogen" refers to fluoro, chloro, bromo, and iodo. "Counterion" is used to represent a small, negatively charged species, such as fluoride, chloride, bromide, iodide, hydroxide, acetate, and sulfate.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

"Extinction coefficient" is a constant used in the Beer-Lambert Law which relates the concentration of the substance being measured (in moles) to the absorbance of the substance in solution (how well the substance in solution blocks light beamed through it from getting out on the other side). It is an indicator of how much light a compound absorbs at a particular wavelength.

In the specification, the singular forms also include the plural, unless the context clearly dictates otherwise. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

"Small molecule" refers to a molecule, which has a molecular weight of less than about 2000 amu, or less than about 1000 amu, and even less than about 500 amu.

All percentages and ratios used herein, unless otherwise indicated, are by weight.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity"). "Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

The term "RAL" means retinaldehyde. "Free RAL" is defined as RAL that is not bound to a visual cycle protein. The terms "trans-RAL" and "all-trans-RAL" are used interchangeably and mean all-trans-retinaldehyde.

Embodiments described herein relate to compounds and methods of treating diabetic retinopathy in a subject in need thereof. The methods can include administering to the subject a therapeutically effective amount of one or more agents that can inhibit diabetes induced oxidative stress and retinal capillary degeneration. The one or more agents can act as traps of reactive aldehydes, inhibit degeneration of photoreceptors, and/or inhibit diabetes-induced superoxide generation and capillary degeneration regulated by GPCR signaling pathways.

It was found that extracellular GPCRs contribute to superoxide generation by the retina in diabetes. When binding to appropriate ligands, GPCRs transduce extracellular stimuli into intracellular second messengers through activation of one or several G proteins, including the Gs, Gi, and Gq subtypes. It had previously been found that the Gs subtype activates adenylate cyclase, thus increasing intracellular cAMP, a secondary messenger that signals through activation of PKA or exchange proteins activated by cAMP. In contrast, activation of the Gi subtype inhibits adenylate cyclase and suppresses signaling of the cAMP/PKA pathway. The Gq subtype activates PLC, which increases the second messengers IP3 and diacylglycerol. Water-soluble IP3 diffuses through the cytoplasm into the ER, where it binds to and opens calcium channels, releasing calcium stores into the cytoplasm. Ionized calcium affects many cellular processes, including activation of NADPH oxidase, an enzyme capable of generating large amounts of superoxide.

These discoveries show that important lesions of diabetic retinopathy, and other complications of diabetes, can be inhibited by therapies selectively targeting a subset of GPCRs and/or their signaling pathways. Moreover, because all 3 GPCR signaling pathways regulate superoxide generation by retinal cells, combinations of therapies at safe low doses that target several GPCR signaling pathways can inhibit diabetic retinopathy without undesirable side effects.

Moreover, it was found that Ret-$NH_2$ also inhibits early stages of diabetic retinopathy (DR), including increased permeability and degeneration of retinal capillaries. The pathology of DR differs from that of models of retinal degeneration in a number of ways, including the relative sparing of photoreceptors in most diabetic patients and animals, and the lack of accumulation of toxic retinoids such as all-trans-retinal and its metabolites. Thus, the observed beneficial effects of Ret-NH$_2$ in diabetes are unlikely to result from these mechanisms.

In some embodiments, the one or more agents that can act as traps of reactive aldehydes, inhibit degeneration of photoreceptors, and/or inhibit diabetes-induced superoxide generation and capillary degeneration regulated by GPCR signaling pathways can include a primary amines that can act as a trap of reactive aldehyde in the retina, retinylamines, retinylamine derivatives, retinoid derivatives, agents that inhibit and/or antagonize the Gq signaling cascade (e.g., agents that inhibit or antagonize Gq-protein coupled receptor activation, alpha 1 adrenergic receptor ($\alpha_1$-AR) activation, PLC activation, IP$_3$ binding to its receptor, Ca+ accumulation in mitochondria, and NADPH oxidase activation), agents that inhibit or antagonize the Gs signaling cascade (e.g., agents that inhibit and/or antagonize Gs-protein coupled receptor activation, 5-HT$_{2a}$ receptor activation, 5-HT$_{2b}$ receptor activation, 5-HT$_{2c}$ receptor activation, 5-HT$_{2a/c}$ receptor activation, 5-HT$_4$ receptor activation, 5-HT$_6$ receptor activation, and 5-HT$_7$ receptor activation, and andenylyl cyclase activation) and/or agents that activate Gi signaling cascade in a retina cell (e.g., Gi-protein coupled receptor agonists, alpha-2 adrenergic receptor agonists, and PKA activators). These agents can be used alone and/or in combination with each other at subtherapeutic doses as well as with other agents to treat diabetic retinopathy.

In some embodiments, the agent can include at least one, two, three, or four or more of a primary amine that can act as a trap of reactive aldehyde in the retina, retinylamines, retinylamine derivatives, retinoid derivatives, an alpha 1 adrenergic receptor ($\alpha_1$-AR) antagonist, a PLC inhibitor, an IP$_3$ receptor inhibitor, an inhibitor of Ca+ accumulation in mitochondria, a NADPH oxidase inhibitor, a 5-HT$_{2a}$ receptor antagonist, a 5-HT$_{2b}$ receptor antagonist, a 5-HT$_{2c}$ receptor antagonist, a 5-HT$_{2a/c}$ receptor antagonist, a 5-HT$_4$ receptor antagonist, a 5-HT$_6$ receptor antagonist, 5-HT$_7$ receptor antagonist, andenylyl cyclase inhibitor, an M3 receptor antagonist, an alpha-2 adrenergic receptor agonists, or a PKA activator.

Figure 2:
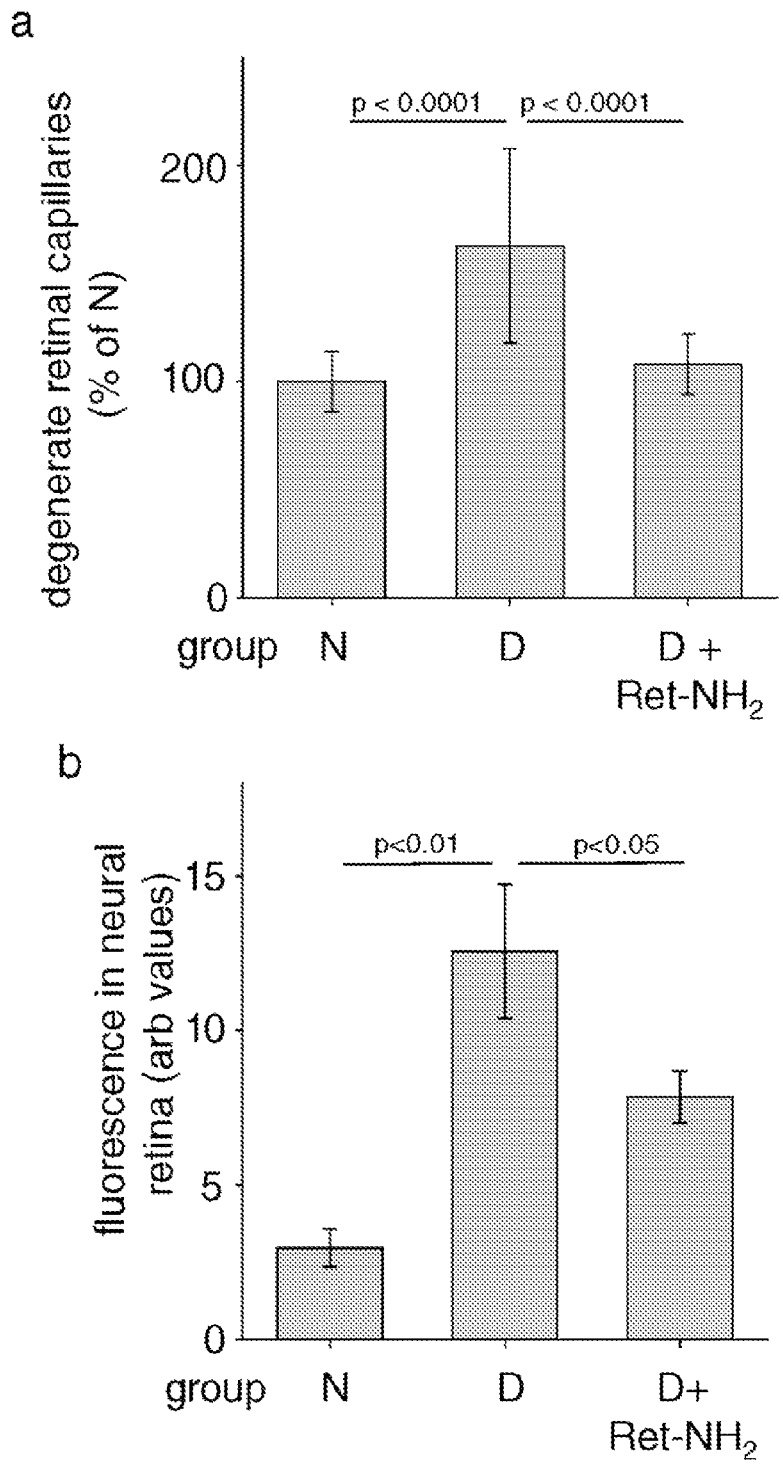
FIGS. 2(A-B) illustrate graphs showing administration of Ret-NH$_2$ significantly inhibited lesions characteristic of DR. Diabetes of 8 months duration in mice significantly increased (A), degeneration of retinal capillaries and (B), accumulation of FITC-albumin in the neural retina. Ret-NH$_2$ (0.2 mg per mouse) administered once per week from the onset of diabetes significantly reduced both of these lesions. Vascular histopathology was quantitated microscopically following isolation of the vasculature by the elastase digestion method. Fluorescence in the neural retina was assessed following intravenous injection of FITC-BSA. (panel a, n=8 in all groups; panel b, n=5-7 in all groups).
Figure 10:
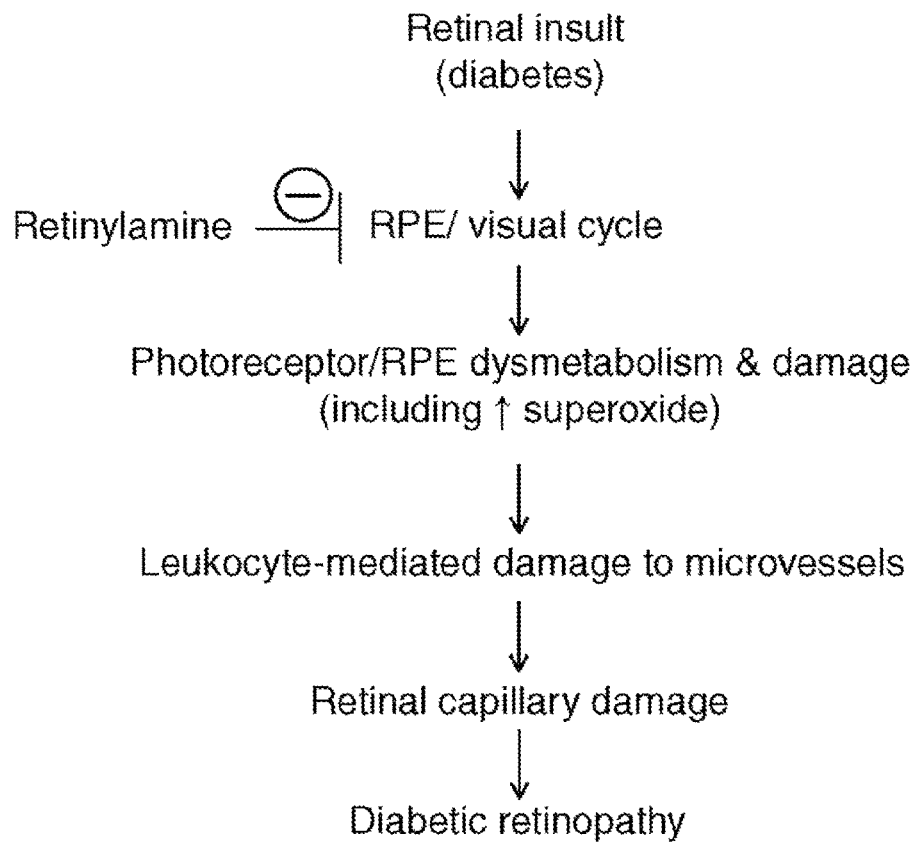
FIG. 10 illustrates a schematic of a postulated mechanism by which weekly injections of Ret-NH$_2$ protect against the vascular lesions of diabetic retinopathy.
Figure 12:
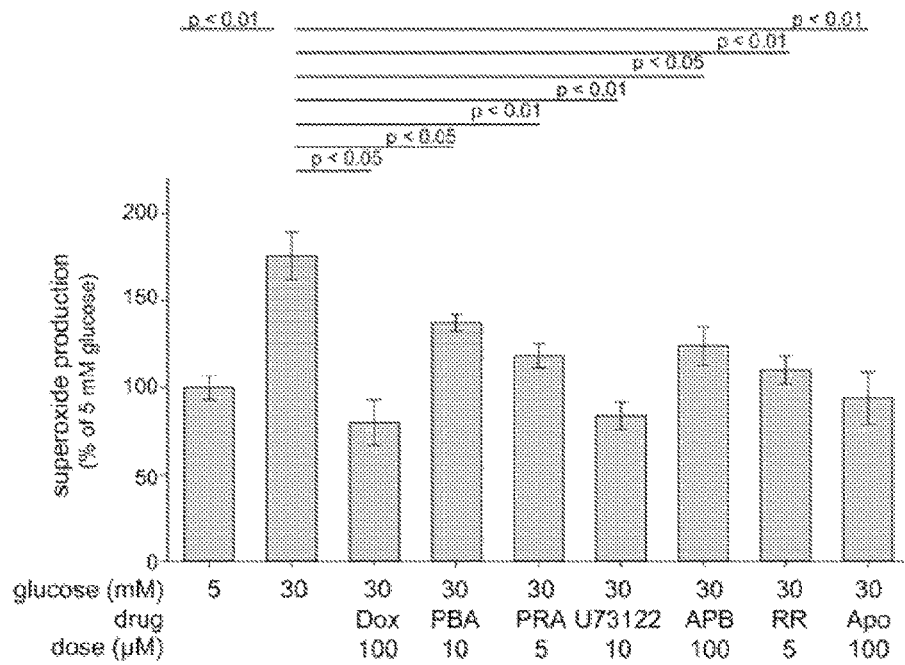
FIG. 12 illustrates a graph showing pharmacological inhibition of the $\alpha_1$-AR and Gq pathway (including downstream PLC, IP3, $Ca^{2+}$, and NADPH oxidase) decreased superoxide formation in 661W cells. Cells were incubated for 4 days in 30 mM glucose in the presence of therapies at the concentrations listed. Then cells were harvested, concentrated by centrifugation, and assayed for superoxide by the lucigenin method. Dox, PBA (phenoxybenzamine), and PRA (prazosin) are $\alpha_1$-AR antagonists. Other drugs tested were U73122 (a PLC inhibitor); APB, (2-APB or 2-aminoethoxydiphenyl borate, an inhibitor of IP3-induced Ca2+ release); RR (ruthenium red, a $Ca^{2+}$ release inhibitor); and Apo (apocynin, a NADPH oxidase inhibitor).
Figure 14:
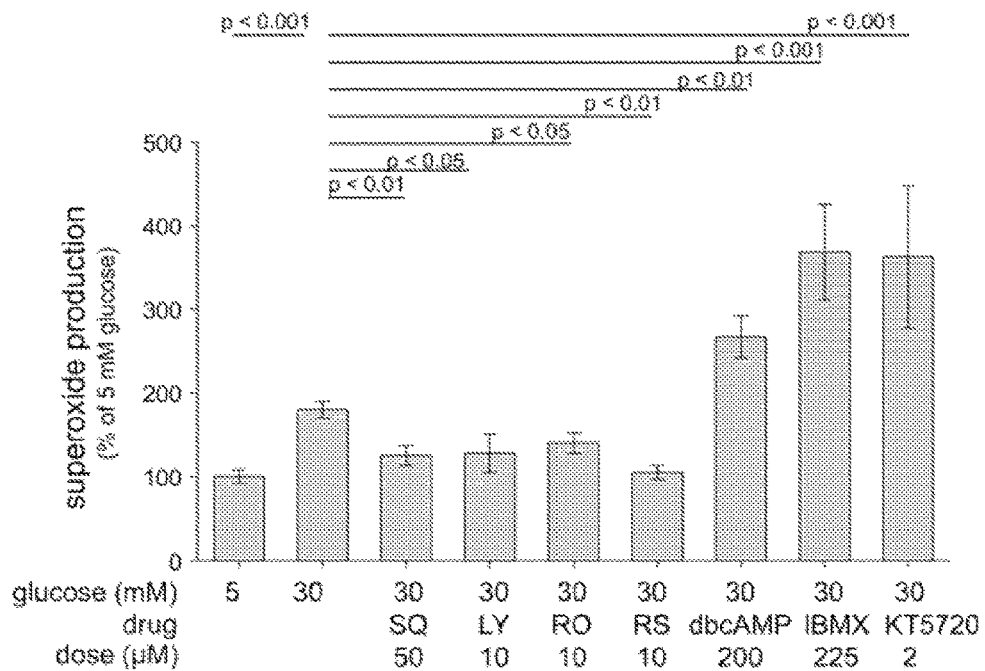
FIG. 14 illustrates a graph showing pharmacologic inhibition of Gs-coupled 5-HTRs lowered superoxide formation in 661W cells incubated for 4 days in 30 mM glucose, whereas a cAMP analog (db cAMP, dibutyryl cAMP), a phosphodiesterase inhibitor (IBMX), or a PKA inhibitor (KT5720) increased it. SQ, SQ 22536, an adenylate cyclase inhibitor; LY, LY 215840, a 5-HT2R/5-HT7R antagonist; RO, RO 04-6790, a 5-HT6R antagonist; RS, RS 23597-190, a 5-HT4R antagonist.
Figure 17:
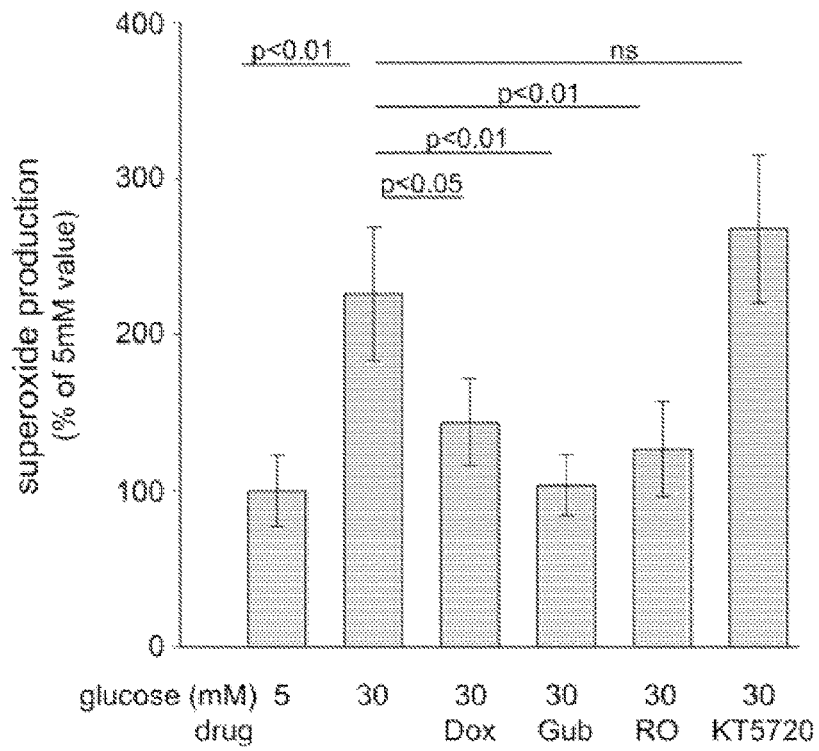
FIG. 17 illustrates a graph showing the effect of therapies on retinal explants ex vivo. Pharmacologic inhibition of the $\alpha_1$-AR and Gq pathways in retinal explants decreased superoxide generation by retinas from nondiabetic mice incubated 4 days in 30 mM glucose, whereas inhibition of cAMP-regulated protein kinase (PKA) failed to reduce superoxide production. Dox, doxazosin; Gub, guanabenz; RO, RO 04-6790, a 5-HT6R antagonist; KT5720, a PKA inhibitor.
Figure 18:
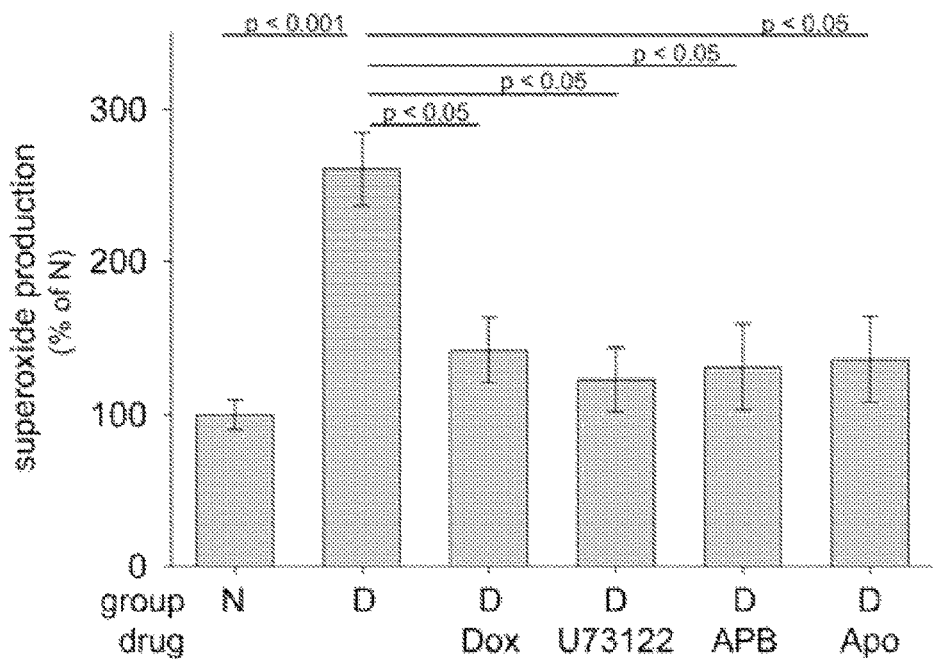
FIG. 18 illustrates a graph showing two months of diabetes in mice (D) increased retinal superoxide production compared with nondiabetic mice (N) through a GPCR/PLC/IP3/Ca2+/NADPH oxidase signaling cascade, and inhibition of any of these downstream steps reduced the excess superoxide generation by isolated retina. Dox (10 mg/kg BW), U73122 (6.25 mg/kg BW), APB (2-APB; 6.25 mg/kg BW), and Apo (36 mg/kg BW) were injected i.p. in DMSO daily for the 2 months of diabetes.
Figure 19:
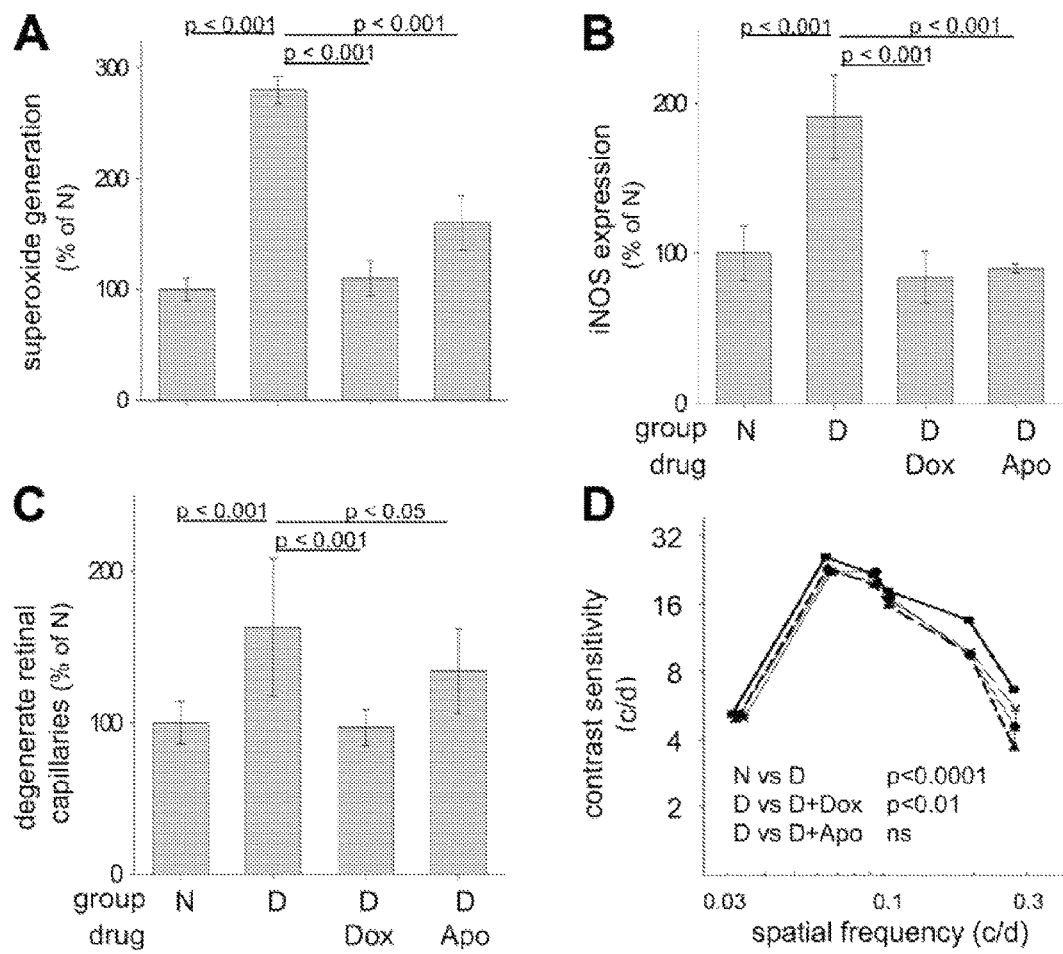
FIGS. 19(A-D) illustrates graphs and a plot showing daily administration of inhibitors of $\alpha_1$-ARs (Dox) and NADPH oxidase (Apo) for 8 months to mice significantly reduced diabetes induced increases in retinal superoxide (A), expression of iNOS (B), and capillary degeneration (C). Dox (but not Apo) significantly inhibited the diabetes-induced defect in contrast sensitivity at 8 months of diabetes, but the functional effect was modest (D). Nondiabetic, solid squares, solid line; diabetic, solid triangles, dashed line; diabetic+doxazosin, solid circles, thin solid line; diabetic+apocynin, X, thin solid line. Contrast sensitivity was determined at the same spatial frequencies in all groups, but group means are offset slightly to allow easier visualization of the data.

By way of example, FIGS. 2 and 12 show primary amine, Ret-NH$_2$ and alpha 1 adrenergic receptor antagonists, such as doxazosin, can inhibit diabetes-induced superoxide generation and capillary degeneration. FIG. 10 shows the relationship of major GPCR signaling pathways (Gs, Gi, and Gq) to superoxide generation and drugs used in vitro to test these relationships. FIG. 12 shows pharmacological inhibition of the α1-AR and Gq pathway using α1-AR antagonists (doxazosin (Dox), PBA (phenoxybenzamine), and PRA (prazosin)), U73122 (a PLC inhibitor), APB, (2-APB or 2-aminoethoxydiphenyl borate, an inhibitor of IP3-induced Ca2+ release); RR (ruthenium red, a Ca2+ release inhibitor); and Apo (apocynin, a NADPH oxidase inhibitor), decreased superoxide formation in 661W cells. FIG. 14 shows pharmacologic inhibition of Gs-coupled 5-HTRs using serotonin receptor antagonists, LY 215840 (LY, a 5-HT2R/5-HT7R antagonist), RO 04-6790 (RO, a 5-HT6R antagonist), and RS 23597-190 (RS, a 5-HT4R antagonist), lowered superoxide formation in 661W cells incubated for 4 days in 30 mM glucose, whereas a cAMP analog (db cAMP, dibutyryl cAMP), a phosphodiesterase inhibitor (IBMX), or a PKA inhibitor (KT5720) increased it. FIG. 15 shows pharmacologic activation of α2-ARs (Gi pathway) inhibited the glucose-induced increase in superoxide generation by 661W cells. FIG. 16 shows combinations of suboptimal doses of compounds that act on different G protein signaling pathways show additive effects on superoxide inhibition in 661W cells. Simultaneous inhibition of the Gq and Gs pathways with Dox and RO (RO-04-6790) or inhibition of the Gi and activation of the Gq pathways with Dox and Gub resulted in greater suppression of superoxide generation than single therapies. FIG. 17 shows pharmacologic inhibition of the α1-AR and Gq pathways in retinal explants decreased superoxide generation by retinas from nondiabetic mice incubated 4 days in 30 mM glucose, whereas inhibition of cAMP-regulated protein kinase (PKA) failed to reduce superoxide production. FIG. 18 shows two months of diabetes in mice (D) increased retinal superoxide production compared with nondiabetic mice (N) through a GPCR/PLC/IP3/Ca2+/NADPH oxidase signaling cascade, and inhibition of any of these downstream steps reduced the excess superoxide generation by isolated retina. FIG. 19 show daily administration of inhibitors of α$_1$-ARs (Dox) and NADPH oxidase (Apo) for 8 months to mice significantly reduced diabetes induced increases in retinal superoxide (A), expression of iNOS (B), and capillary degeneration (C). Dox (but not Apo) significantly inhibited the diabetes-induced defect in contrast sensitivity at 8 months of diabetes, but the functional effect was modest (D).

In other embodiments, diabetic retinopathy in a subject can be treated by administering the subject at least one primary amines that can act as a trap of reactive aldehyde in the retina, in combination with retinylamines, retinylamine derivatives, or retinoid derivatives, and/or at least one agent that can inhibit and/or antagonize the Gq signaling cascade (e.g., agents that inhibit or antagonize Gq-protein coupled receptor activation, alpha 1 adrenergic receptor ($\alpha_1$-AR) activation, PLC activation, IP$_3$ binding to its receptor, Ca+ accumulation in mitochondria, and NADPH oxidase activation), and/or at least one agent that can inhibit or antagonize the Gs signaling cascade (e.g., agents that inhibit and/or antagonize Gs-protein coupled receptor activation, 5-HT$_{2a}$ receptor activation, 5-HT$_{2b}$ receptor activation, 5-HT$_{2c}$ receptor activation, 5-HT$_{2a/c}$ receptor activation, 5-HT$_4$ receptor activation, 5-HT$_6$ receptor activation, and 5-HT$_7$ receptor activation, and adenylyl cyclase activation) and/or at least one agent that can activate Gi signaling cascade in a retina cell (e.g., Gi-protein coupled receptor agonists, alpha-2 adrenergic receptor agonists, and PKA activators). These agents when used in combination can be administered at suboptimal or subtherapeutic doses.

In some embodiments, agents used to treat diabetic retinopathy can include Gs receptor antagonists, such as serotonin receptor antagonist. The serotonin receptor antagonist can include 5-HT$_{2a}$ receptor antagonists, 5-HT$_{2b}$ receptor antagonists, 5-HT$_{2c}$ receptor antagonists, 5-HT$_{2a/c}$ receptor antagonists, 5-HT$_4$ receptor antagonists, 5-HT$_6$ receptor antagonists, and 5-HT$_7$ receptor antagonists.

Examples of serotonin receptor antagonists are citalopram, escitalopram, fluoxetine, R-fluoxetine, sertraline, paroxetine, fluvoxamine, venlafaxine, duloxetine, dapoxetine, nefazodone, imipramine, imipramine N-oxide, desipramine, pirandamine, dazepinil, nefopam, befuraline, fezolamine, femoxetine, clomipramine, cianoimipramine, litoxetine, cericlamine, seproxetine, WY 27587, WY 27866, imeldine, ifoxetine, tiflucarbine, viqualine, milnacipran, bazinaprine, YM 922, S 33005, F 98214-TA, OPC 14523, alaproclate, cyanodothepine, trimipramine, quinupramine, dothiepin, amoxapine, nitroxazepine, McN 5652, McN 5707, O1 77, Org 6582, Org 6997, Org 6906, amitriptyline, amitriptyline N-oxide, nortriptyline, CL 255.663, pirlindole, indatraline, LY 113.821, LY 214.281, CGP 6085 A, RU 25.591, napamezole, diclofensine, trazodone, EMD 68.843, BMY 42.569, NS 2389, sercloremine, nitroquipazine, ademethionine, sibutramine, clovoxamine, desmethylsubitramine, didesmethylsubitramine, clovoxamine vilazodone, N-[(1-[(6-Fluoro-2-napthalenyl)methyl]-4-piperidinyl]amino]carbonyl]-3-pyridine carboxamide, [trans-6-(2-chlorophenyl)-1,2,3,5,6,10b-hexahydropyrrolo-(2,1-a)isoquinol-ine] (McN 5707), (dl-4-exo-amino-8-chloro-benzo-(b)-bicyclo [3.3.1] nona-2-6 alpha (10 alpha)-diene hydrochloride) (Org 6997), (dl)-(5 alpha,8 alpha,9 alpha)-5,8,9,10-Tetrahydro-5,9-methanobenzocycloocten-8-amine hydrochloride (Org 6906), -[2-[4[(6-fluoro-1H-indol-3-yl)-3,6-dihydro-1(2H)-pyridinyl]ethyl]-3-isop-ropyl-6-(methylsulphonyl)-3,4-dihydro-1H-2,1,3-benzothiadiazine-2,2-dioxid-e (LY393558), [4-(5,6-dimethyl-2-benzofuranyl)-piperidine] (CGP 6085), dimethyl-[5-(4-nitro-phenoxy)-6,7,8,9-tetrahydro-5H-benzocyclohepten-7-yl-]amine (RU 25.591), or a pharmaceutically acceptable salt of any of these compounds.

In one embodiment, the serotonin receptor antagonist is selected from agomelatine, pizotifen, RS 23579-190, Ro 04-6790 (4-Amino-N-[2,6-bis(methylamino)-4-pyrimidinyl]benzenesulfonamidev), SGS 518 oxalate (1-methyl-3-(1-methyl-4-piperidyl)indol-5-yl] 2,6-difluorobenzenesulfonate; oxalic acid), SB 269970 (3-({(2R)-2-[2-(4-Methyl-1-piperidinyl)ethyl]-1-pyrrolidinyl}sulfonyl)phenol hydrochloride (1:1)), LY 215840 ((8β)-N-[(1S,2R)-2-Hydroxycyclopentyl]-1-isopropyl-6-methylergoline-8-carboxamide), citalopram, escitalopram, fluoxetine, sertraline, paroxetine, fluvoxamine, venlafaxine, duloxetine, dapoxetine, nefazodone, imipramine, femoxetine and clomipramine or a pharmaceutically acceptable salt of any of these compounds.

In other embodiments, the agent can include a 5-HT$_{2a}$ receptor antagonist. Examples of 5-HT$_{2a}$ receptor antagonists are described in U.S. Pat. No. 4,444,778 and can include nefazodone, pizotifen, ketanserin, desipramine, imipramine, chlorimipramine, protriptylene, dibenzepine, amitryptyline, doxepin, prothiadene, pirandamine, spirobenzofuran, ciclazindol, nefopam, deximafen, daledalin, amedalin, quipazine, trazodone, zimelidine, tofenacine, fenetazole and fenflurame. Additional compounds which have 5-HT$_{2a}$ antagonist activity and can be used are 11-amino-1,5-methano-1,2,5,6-tetrahydrobenzocine; 1-methylamino-4-phenyl-1,2,3,4-tetrahydronaphthylene; 6-cyano-1,3-dihydro-3-dimethylaminopropyl-3-(p-fluorophenyl)-isobenzofuran; 4-benzyl-1-(2-benzofurancarbonyl)-piperidide, 1,4-ethano-4-phenyl-cyclohexylamine, α-(p-chlorophenyl)-2-methylaminomethylbenzyl alcohol; α-(2-methylaminoethyl)-2-methoxy or 4-trifluoromethylphenylbenzyl ether or p-anisyl-(1-methyl-4-phenyl-3-pipecolinyl)-ether. Still other examples of 5-HT$_{2a}$ receptor antagonists include piperidinylamino-thieno[2,3-d]pyrimidine compounds described in U.S. Pat. No. 7,030,240 and 1,4-substituted cyclic amine derivatives described in U.S. Pat. No. 7,541,371

In other embodiments, agents used to treat diabetic retinopathy can include G$_q$ receptor antagonists, such as alpha 1 adrenergic receptor antagonists. Examples of alpha 1 adrenergic receptor antagonists that can be used to treat ocular disorders described herein include phentolamine family antagonists, known as imidazolines, alkylating agents such as phenoxybenzamine, or piperazinyl quinazolines.

In specific embodiments, the alpha 1 adrenergic receptor antagonist can include, for example, doxazosin, prazosin, tamsulosin, terazosin, phenxoxybenzamine, and 5-methylurapadil. The syntheses of these compounds are described in U.S. Pat. Nos. 3,511,836, 3,957,786, 4,026,894, 5,798,362, 5,792,767, 5,891,882, 5,959,108, and 6,046,207. Additionally, other alpha 1 adrenergic receptor antagonist are well known in the art. See, for example, Lagu, "Identification of alpha 1A-adrenoceptor selective antagonists for the treatment of benign prostatic hyperplasia", Drugs of the Future 2001, 25(8), 757-765 and Forray et al., 8 Exp. Opin. Invest. Drugs 2073 (1999), hereby incorporated by reference in its entirety, which provide examples of numerous alpha 1 adrenergic receptor antagonists.

In other embodiments, agents used to treat diabetic retinopathy can include alpha-2 adrenergic receptor agonists that can activate the Gi signaling cascade and inhibit andenylyl cyclase activity. Examples of alpha-2 adrenergic receptor agonists include L-norepinephrine, clonidine, dexmetdetomidine, apraclonidine, methyldopa, tizanidine, brimonidine, xylometazoline, tetrahydrozoline, oxymetazoline, guanfacine, guanabenz, guanoxabenz, guanethidine, xylazine, medetomide, moxonidine, mivazerol, rilmenidine, UK 14,304, B-HT 933, B-HT 920, octopamine or a combination thereof.

Other examples of alpha-2 adrenergic receptor agonists include, but are not limited to amidephrine, amitraz, anisodamine, apraclonidine, cirazoline, detomidine, epinephrine, ergotamine, etilefrine, indanidine, lofexidine, medetomidine, mephentermine, metaraminol, methoxamine, midodrine, naphazoline, norepinephrine, norfenefrine, octopamine, oxymetazoline, phenylpropanolamine, rilmenidine, romifidine, synephrine, talipexole, tizanidine, or a combination thereof.

In still other embodiments, agents used to treat diabetic retinopathy can include an adenylyl cyclase inhibitor. Examples of adenylyl cyclase inhibitors are 9-tetrahydrofuryl adenine, such as THFA or SQ 22536, 2',5'-dideoxyadenosine, or 9-(cyclopentyl)-adenine.

In another embodiment, the agent can include a M3 receptor antagonist, such as 4-DAMP or tolterodine. Other examples of M3 receptor antagonists are described in U.S. Pat. Nos. 7,723,356, 7,361,648, and 7,947,730.

In another embodiment, the agent can include a phospholipase C (PLC) inhibitor. Examples of PLC inhibitors are described in U.S. Pat. No. 6,235,729 and can include U73122 (1-(6-((17β-3-methoxyestra-1,3,5(10)-trien-17-yl)amino)hexyl)-1H-pyrrole-2,5-dione), ET-18-OCH$_3$ (1-O-octadecyl-2-O-methyl-sn-glycero-3-phosphorylcholine), and RHC-80267 (1,6-bis-(cyclohexyloximinocarbonylamino)-hexane). Still other examples of PLC inhibitors can include α-hydroxyphosphonate compounds described in U.S. Pat. No. 5,519,163.

In still other embodiments, the agents can include NADPH oxidase inhibitors, such as apocynin (1-(4-hydroxy-3-methoxyphenylethanone) or diacylglycerols) and agents that selectively target aberrant all-trans-retinal accumulation in the retina.

Examples of agents that selectively target all-trans-retinal accumulation are described in PCT/US2010/059426 and can include primary amines (i.e., primary amine compounds) that form reversible Schiff-bases with free all-trans-RAL, which has escaped sequestering in photoreceptor outer segments of the retina without adversely affecting normal retinoid cycle.

In an embodiment of the application, the primary amine compounds that can form stable Schiff-bases with all-trans-RAL under physiological conditions of the retina and that can inhibit retinal degeneration upon administration to a subject can be selected using an in vitro assay that measures the ability of a primary amine compound to form a Schiff base with retinal under physiological condition of the retina and in vivo assays that measure, respectively, 11-cis-retinal formation and the optical coherence tomography score of retinas of Rdh8$^{-/-}$Abca4$^{-/-}$ mice. Primary amine compounds that form a Schiff-base with all-trans-RAL or its metabolite under physiologic conditions of the retina and that when administered to a Rdh8$^{-/-}$Abca4$^{-/-}$ mouse increase the optical coherence tomography score of the mouse to at least about 2.5 and increase 11-cis-retinal amount at least about 30% in comparison to untreated control animal are effective in treating retinal degeneration in a subject associated with aberrant all-trans-RAL clearance. Primary amines compounds that do not form a form a Schiff-base with all-trans-RAL or its metabolite under physiologic conditions of the retina or which when administered to a Rdh8$^{-/-}$Abca4$^{-/-}$ mouse do not increase the optical coherence tomography score of the mouse to at least about 2.5 and increase 11-cis-retinal amount at least about 30% in comparison to untreated control animal, were found to be ineffective in treating retinal degeneration in a subject associated with aberrant all-trans-RAL clearance. Additionally, therapeutic efficacy of the primary amine compounds of the application can be determined using an in vitro assay that measures the ability of a primary amine compound to improve viability of RPE cells treated with retinal.

In some embodiments, the primary amine compound can include the structural formula (VIII):

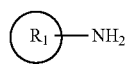
(VIII)

wherein $R_1$ is an aliphatic and/or aromatic compound.

Primary amine compounds having formula I that are used to treat retinal degeneration in accordance with an embodiment of the application can upon administration to the subject form a reversible Schiff-base with the all-trans-RAL without adversely affecting normal retinoid cycle performance and when administered to a Rdh8$^{-/-}$Abca4$^{-/-}$ mouse increase the optical coherence tomography score of the mouse to at least about 2.5 and increase 11-cis-retinal amount at least about 30% in comparison to untreated control animal. Primary amine compounds in accordance with the application, however, do not include and are not a local anesthetic, which includes an aromatic amine that demonstrates sodium channel blockade when administered to the subject.

Advantageously, the primary amine compounds in accordance with the application do not inhibit RPE65 enzymatic activity or any other proteins involved in retinoid metabolism in the eye of the subject. The primary amine compounds can reduce the formation of A2E and/or retinal dimer in the subject's retina, promote 11-cis-retinal production in the subject, and does not cause night blindness.

In some embodiments, primary compounds having formula I that upon administration to a subject form a reversible Schiff-base with the all-trans-RAL without adversely affecting normal retinoid cycle performance and that when administered to a Rdh8$^{-/-}$Abca4$^{-/-}$ mouse increase the optical coherence tomography score of the mouse to at least about 2.5 and increase 11-cis-retinal amount at least about 30% in comparison to untreated control animal.

In some embodiments, the primary amine compound is a compound having the following structural formula:

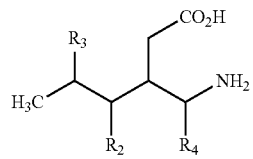

wherein $R_2$ is hydrogen or ($C_1$-$C_6$) straight chain or branched unsubstituted or substituted alkyl;
$R_3$ is straight or branched unsubstituted or substituted alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl, OH, -alkylphenyl, -alkylphenoxy, -phenyl or substituted phenyl;
$R_4$ is hydrogen or ($C_1$-$C_6$) straight chain or branched unsubstituted or substituted alkyl, or carboxyl;
as well as pharmaceutically acceptable salts thereof.

In other embodiments, the primary amine compound is a compound having the following structural formula:

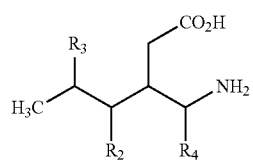

wherein $R_2$ is hydrogen, straight or branched alkyl of from 1 to 6 carbon atoms or phenyl;
$R_3$ is straight or branched alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl OH-alkylphenyl, -alkylphenoxy, -phenyl or substituted phenyl; and
$R_4$ is hydrogen, and $R_2$ is straight or branched alkyl of from 1 to 6 carbon atoms or phenyl when $R_3$ is methyl, or a pharmaceutically acceptable salt thereof.

In other embodiments, the primary amine compound can have the following structural formula:

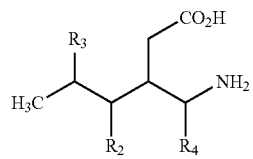

wherein $R_2$ is methyl, $R_3$ is an alkyl, and $R_4$ is a hydrogen, or a pharmaceutically acceptable salt thereof.

Specific examples of compounds of above noted formulas are selected from: 3-Aminomethyl-5-methylhexanoic acid; 3-Aminomethyl-5-methylheptanoic acid; 3-Aminomethyl-5-methyl-octanoic acid; 3-Aminomethyl-5-methyl-nonanoic acid; 3-Aminomethyl-5-methyl-decanoic acid; 3-Aminomethyl-5-methyl-undecanoic acid; 3-Aminomethyl-5-methyl-dodecanoic acid; 3-Aminomethyl-5-methyl-tridecanoic acid; 3-Aminomethyl-5-cyclopropyl-hexanoic acid; 3-Aminomethyl-5-cyclobutyl-hexanoic acid; 3-Aminomethyl-5-cyclopentyl-hexanoic acid; 3-Aminomethyl-5-cyclohexyl-hexanoic acid; 3-Aminomethyl-5-trifluoromethylhexanoic acid; 3-Aminomethyl-5-phenyl-hexanoic acid; 3-Aminomethyl-5-(2-chlorophenyl)-hexanoic acid; 3-Aminomethyl-5-(3-chlorophenyl)-hexanoic acid; 3-Aminomethyl-5-(4-chlorophenyl)-hexanoic acid; 3-Aminomethyl-5-(2-methoxyphenyl)-hexanoic acid; 3-Aminomethyl-5-(3-methoxyphenyl)-hexanoic acid; 3-Aminomethyl-5-(4-methoxyphenyl)-hexanoic acid; 3-Aminomethyl-5-(phenylmethyl)-hexanoic acid; (S)-3-(Aminomethyl)-5-methylhexanoic acid; (R)-3-(Aminomethyl)-5-methylhexanoic acid; (3R,4S)-3-Aminomethyl-4,5-dimethyl-hexanoic acid; 3-Aminomethyl-4,5-dimethyl-hexanoic acid; (3R,4S)-3-Aminomethyl-4,5-dimethyl-hexanoic acid MP; (3S,4S)-3-Aminomethyl-4,5-dimethyl-hexanoic acid; (3R,4R)-3-Aminomethyl-4,5-dimethyl-hexanoic acid MP; 3-Aminomethyl-4-isopropyl-hexanoic acid; 3-Aminomethyl-4-isopropyl-heptanoic acid; 3-Aminomethyl-4-isopropyl-octanoic acid; 3-Aminomethyl-4-isopropyl-nonanoic acid; 3-Aminomethyl-4-isopropyl-decanoic acid; 3-Aminomethyl-4-phenyl-5-methyl-hexanoic acid; (3S,5S)-3-Aminomethyl-5-methoxy-hexanoic acid; (3S,5S)-3-Aminomethyl-5-ethoxy-hexanoic acid; (3S,5S)-3-Aminomethyl-5-propoxy-hexanoic acid; (3S,5S)-3-Aminomethyl-5-isopropoxy-hexanoic acid; (3S,5S)-3-Aminomethyl-5-tert-butoxy-hexanoic acid; (3S,5S)-3-Aminomethyl-5-fluoromethoxy-hexanoic acid; (3S,5S)-3-Aminomethyl-5-(2-fluoro-ethoxy)-hexanoic acid; (3S,5S)-3-Aminomethyl-5-(3,3,3-trifluoro-propoxy)-hexanoic acid; (3S,5S)-3-Aminomethyl-5-phenoxy-hexanoic acid; (3S,5S)-3-Aminomethyl-5-(4-chloro-phenoxy)-hexanoic acid; (3S,5S)-3-Aminomethyl-5-(3-chloro-phenoxy)-hexanoic acid; (3S,5S)-3-Aminomethyl-5-(2-chloro-phenoxy)-hexanoic acid; (3S,5S)-3-Aminomethyl-5-(4-fluoro-phenoxy)-hexanoic acid; (3S,5S)-3-Aminomethyl-5-(3-fluoro-phenoxy)-hexanoic acid; (3S,5S)-3-Aminomethyl-5-(2-fluoro-phenoxy)-hexanoic acid; (3S,5S)-3-Aminomethyl-5-(4-methoxy-phenoxy)-hexanoic acid; (3S,5S)-3-Aminomethyl-5-(3-methoxy-phenoxy)-hexanoic acid; (3S,5S)-3-Aminomethyl-5-(2-methoxy-phenoxy)-hexanoic acid; (3S,5S)-3-Aminomethyl-5-(4-nitro-phenoxy)-hexanoic acid; (3S,5S)-3-Aminomethyl-5-(3-nitro-phenoxy)-hexanoic acid; (3S,5S)-3-Aminomethyl-5-(2-nitro-phenoxy)-hexanoic acid; (3S,5S)-3-Aminomethyl-6-hydroxy-5-methyl-hexanoic acid; (3S,5S)-3-Aminomethyl-6-methoxy-5-methyl-hexanoic acid; (3S,5S)-3-Aminomethyl-6-ethoxy-5-methyl-hexanoic acid; (3S,5S)-3-Aminomethyl-5-methyl-6-propoxy-hexanoic acid; (3S,5S)-3-Aminomethyl-6-isopropoxy-5-methyl-hexanoic acid; (3S,5S)-3-Aminomethyl-6-tert-butoxy-5-methyl-hexanoic acid; (3S,5S)-3-Aminomethyl-6-fluoromethoxy-5-methyl-hexanoic acid; (3S,5S)-3-Aminomethyl-6-(2-fluoro-ethoxy)-5-methyl-hexanoic acid; (3S,5S)-3-Aminomethyl-5-methyl-6-(3,3,3-trifluoro-propoxy)-hexanoic acid; (3S,5S)-3-Aminomethyl-5-methyl-6-phenoxy-hexanoic acid; (3S,5S)-3-Aminomethyl-6-(4-chloro-phenoxy)-5-methyl-hexanoic acid; (3S,5S)-3-Aminomethyl-6-(3-chloro-phenoxy)-5-methyl-hexanoic acid; (3S,5S)-3-Aminomethyl-6-(2-chloro-phenoxy)-5-methyl-hexanoic acid; (3S,5S)-3-Aminomethyl-6-(4-fluoro-phenoxy)-5-methyl-hexanoic acid; (3S,5S)-3-Aminomethyl-6-(3-fluoro-phenoxy)-5-methyl-hexanoic acid; (3S,5S)-3-Aminomethyl-6-(2-fluoro-phenoxy)-5-methyl-hexanoic acid; (3S,5S)-3-Aminomethyl-6-(4-methoxy-phenoxy)-5-methyl-hexanoic acid; (3S,5S)-3-Aminomethyl-6-(3-methoxy-phenoxy)-5-methyl-hexanoic acid; (3S,5S)-3-Aminomethyl-6-(2-methoxy-phenoxy)-5-methyl-hexanoic acid; (3S,5S)-3-Aminomethyl-5-methyl 6-(4-trifluoromethyl-phenoxy)-hexanoic acid; (3S,5S)-3-Aminomethyl-5-methyl 6-(3-trifluoromethyl-phenoxy)-hexanoic acid; (3S,5S)-3-Aminomethyl-5-methyl 6-(2-trifluoromethyl-phenoxy)-hexanoic acid; (3S,5S)-3-Aminomethyl-5-methyl 6-(4-nitro-phenoxy)-hexanoic acid; (3S,5S)-3-Aminomethyl-5-methyl 6-(3-nitro-phenoxy)-hexanoic acid; (3S,5S)-3-Aminomethyl-5-methyl 6-(2-nitro-phenoxy)-hexanoic acid; (3S,5S)-3-Aminomethyl-6-benzyloxy-5-methyl-hexanoic acid; (3S,5S)-3-Aminomethyl-7-hydroxy-5-methyl-heptanoic acid; (3S,5S)-3-Aminomethyl-7-methoxy-5-methyl-heptanoic acid; (3S,5S)-3-Aminomethyl-7-ethoxy-5-methyl-heptanoic acid; (3S,5S)-3-Aminomethyl-5-methyl-7-propoxy-heptanoic acid; (3S,5S)-3-Aminomethyl-7-isopropoxy-5-methyl-heptanoic acid; (3S,5S)-3-Aminomethyl-7-tert-butoxy-5-methyl-heptanoic acid; (3S,5S)-3-Aminomethyl-7-fluoromethoxy-5-methyl-heptanoic acid; (3S,5S)-3-Aminomethyl-7-(2-fluoro-ethoxy)-5-methyl-heptanoic acid; (3S,5S)-3-Aminomethyl-5-methyl-7-(3,3,3-trifluoro-propoxy)-heptanoi-c acid; (3S,5S)-3-Aminomethyl-7-benzyloxy-5-methyl-heptanoic acid; (3S,5S)-3-Aminomethyl-5-methyl-7-phenoxy-heptanoic acid; (3S,5S)-3-Aminomethyl-7-(4-chloro-phenoxy)-5-methyl-heptanoic acid; (3S,5S)-3-Aminomethyl-7-(3-chloro-phenoxy)-5-methyl-heptanoic acid; (3S,5S)-3-Aminomethyl-7-(2-chloro-phenoxy)-5-methyl-heptanoic acid; (3S,5S)-3-Aminomethyl-7-(4-fluoro-phenoxy)-5-methyl-heptanoic acid; (3S,5S)-3-Aminomethyl-7-(3-fluoro-phenoxy)-5-methyl-heptanoic acid; (3S,5S)-3-Aminomethyl-7-(2-fluoro-phenoxy)-5-methyl-heptanoic acid; (3S,5S)-3-Aminomethyl-7-(4-methoxy-phenoxy)-5-methyl-heptanoic acid; (3S,5S)-3-Aminomethyl-7-(3-methoxy-phenoxy)-5-methyl-heptanoic acid; (3S,5S)-3-Aminomethyl-7-(2-methoxy-phenoxy)-5-methyl-heptanoic acid; (3S,5S)-3-Aminomethyl-5-methyl-7-(4-trifluoromethyl-phenoxy)-heptan-oic acid; (3S,5S)-3-Aminomethyl-5-methyl-7-(3-trifluoromethyl-phenoxy)-heptan-oic acid; (3S,5S)-3-Aminomethyl-5-methyl-7-(2-trifluoromethyl-phenoxy)-heptan-oic acid; (3S,5S)-3-Aminomethyl-5-methyl-7-(4-nitro-phenoxy)-heptanoic acid; (3S,5S)-3-Aminomethyl-5-methyl-7-(3-nitro-phenoxy)-heptanoic acid; (3S,5S)-3-Aminomethyl-5-methyl-7-(2-nitro-phenoxy)-heptanoic acid; (3S,5S)-3-Aminomethyl-5-methyl-6-phenyl-hexanoic acid; (3S,5S)-3-Aminomethyl-6-(4-chloro-phenyl)-5-methyl-hexanoic acid; (3S,5S)-3-Aminomethyl-6-(3-chloro-phenyl)-5-methyl-hexanoic acid; (3S,5S)-3-Aminomethyl-6-(2-chloro-phenyl)-5-methyl-hexanoic acid; (3S,5S)-3-Aminomethyl-6-(4-methoxy-phenyl)-5-methyl-hexanoic acid; (3S,5S)-3-Aminomethyl-6-(3-methoxy-phenyl)-5-methyl-hexanoic acid; (3S,5S)-3-Aminomethyl-6-(2-methoxy-phenyl)-5-methyl-hexanoic acid; (3S,5S)-3-Aminomethyl-6-(4-fluoro-phenyl)-5-methyl-hexanoic acid; (3S,5S)-3-Aminomethyl-6-(3-fluoro-phenyl)-5-methyl-hexanoic acid; (3S,5S)-3-Aminomethyl-6-(2-fluoro-phenyl)-5-methyl-hexanoic acid; (3S,5R)-3-Aminomethyl-5-methyl-7-phenyl-heptanoic acid; (3S,5R)-3-Aminomethyl-7-(4-chloro-phenyl)-5-methyl-heptanoic acid; (3S,5R)-3-Aminomethyl-7-(3-chloro-phenyl)-5-methyl-heptanoic acid; (3S,5R)-3-Aminomethyl-7-(2-chloro-phenyl)-5-methyl-heptanoic acid; (3S,5R)-3-Aminomethyl-7-(4-methoxy-phenyl)-5-methyl-heptanoic acid; (3S,5R)-3-Aminomethyl-7-(3-methoxy-phenyl)-5-methyl-heptanoic acid; (3S,5R)-3-Aminomethyl-7-(2-methoxy-phenyl)-5-methyl-heptanoic acid; (3S,5R)-3-Aminomethyl-7-(4-fluoro-phenyl)-5-methyl-heptanoic acid; (3S,5R)-3-Aminomethyl-7-(3-fluoro-phenyl)-5-methyl-heptanoic acid; (3S,5R)-3-Aminomethyl-7-(2-fluoro-phenyl)-5-methyl-heptanoic acid; (3S,5R)-3-Aminomethyl-5-methyl-oct-7-enoic acid; (3S,5R)-3-Aminomethyl-5-methyl-non-8-enoic acid; (E)-(3S,5S)-3-Aminomethyl-5- methyl-oct-6-enoic acid; (Z)-(3S,5S)-3-Aminomethyl-5-methyl-oct-6-enoic acid; (Z)-(3S,5S)-3-Aminomethyl-5-methyl-non-6-enoic acid; (E)-(3S,5S)-3-Aminomethyl-5-methyl-non-6-enoic acid; (E)-(3S,5R)-3-Aminomethyl-5-methyl-non-7-enoic acid; (Z)-(3S,5R)-3-Aminomethyl-5-methyl-non-7-enoic acid; (Z)-(3S,5R)-3-Aminomethyl-5-methyl-dec-7-enoic acid; (E)-(3S,5R)-3-Aminomethyl-5-methyl-undec-7-enoic acid; (3S,5S)-3-Aminomethyl-5,6,6-trimethyl-heptanoic acid; (3S,5S)-3-Aminomethyl-5,6-dimethyl-heptanoic acid; (3S,5S)-3-Aminomethyl-5-cyclopropyl-hexanoic acid; (3S,5S)-3-Aminomethyl-5-cyclobutyl-hexanoic acid; (3S,5S)-3-Aminomethyl-5-cyclopentyl-hexanoic acid; (3S,5S)-3-Aminomethyl-5-cyclohexyl-hexanoic acid; (3S,5R)-3-Aminomethyl-5-methyl-heptanoic acid; (3S,5R)-3-Aminomethyl-5-methyl-octanoic acid; (3S,5R)-3-Aminomethyl-5-methyl-nonanoic acid; (3S,5R)-3-Aminomethyl-5-methyl-decanoic acid; (3S,5R)-3-Aminomethyl-5-methyl-undecanoic acid; (3S,5R)-3-Aminomethyl-5-methyl-dodecanoic acid; (3S,5R)-3-Aminomethyl-5,9-dimethyl-decanoic acid; (3S,5R)-3-Aminomethyl-5,7-dimethyl-octanoic acid; (3S,5R)-3-Aminomethyl-5,8-dimethyl-nonanoic acid; (3S,5R)-3-Aminomethyl-6-cyclopropyl-5-methyl-hexanoic acid; (3S,5R)-3-Aminomethyl-6-cyclobutyl-5-methyl-hexanoic acid; (3S,5R)-3-Aminomethyl-6-cyclopentyl-5-methyl-hexanoic acid; (3S,5R)-3-Aminomethyl-6-cyclohexyl-5-methyl-hexanoic acid; (3S,5R)-3-Aminomethyl-7-cyclopropyl-5-methyl-heptanoic acid; (3S,5R)-3-Aminomethyl-7-cyclobutyl-5-methyl-heptanoic acid; (3S,5R)-3-Aminomethyl-7-cyclopentyl-5-methyl-heptanoic acid; (3S,5R)-3-Aminomethyl-7-cyclohexyl-5-methyl-heptanoic acid; (3S,5R)-3-Aminomethyl-8-cyclopropyl-5-methyl-octanoic acid; (3S,5R)-3-Aminomethyl-8-cyclobutyl-5-methyl-octanoic acid; (3S,5R)-3-Aminomethyl-8-cyclopentyl-5-methyl-octanoic acid; (3S,5R)-3-Aminomethyl-8-cyclohexyl-5-methyl-octanoic acid; (3S,5S)-3-Aminomethyl-6-fluoro-5-methyl-hexanoic acid; (3S,5S)-3-Aminomethyl-7-fluoro-5-methyl-heptanoic acid; (3S,5R)-3-Aminomethyl-8-fluoro-5-methyl-octanoic acid; (3S,5R)-3-Aminomethyl-9-fluoro-5-methyl-nonanoic acid; (3S,5S)-3-Aminomethyl-7,7,7-trifluoro-5-methyl-heptanoic acid; (3S,5R)-3-Aminomethyl-8,8,8-trifluoro-5-methyl-octanoic acid; (3S,5R)-3-Aminomethyl-5-methyl-8-phenyl-octanoic acid; (3S,5S)-3-Aminomethyl-5-methyl-6-phenyl-hexanoic acid; (3S,5R)-3-Aminomethyl-5-methyl-7-phenyl-heptanoic acid; and pharmaceutically acceptable salts thereof. Methods of synthesizing the above noted compounds are described in PCT Patent Application No. WO 00/76958, which is incorporated herein by reference in its entirety.

In other embodiments, the primary amine compound can comprise at least one of (S)-3-(Aminomethyl)-5-methylhexanoic acid or (R)-3-(Aminomethyl)-5-methylhexanoic acid. In still other embodiments, the primary amine compound can include a mixture of (S)-3-(Aminomethyl)-5-methylhexanoic acid and (R)-3-(Aminomethyl)-5-methylhexanoic acid. For example, the primary amine compound can comprise a racemic mixture of (S)-3-(Aminomethyl)-5-methylhexanoic acid and (R)-3-(Aminomethyl)-5-methylhexanoic acid. In other examples, the primary amine compound can comprise a mixture of: less than about 50% by weight (S)-3-(Aminomethyl)-5-methylhexanoic acid and greater than about 50% by weight (R)-3-(Aminomethyl)-5-methylhexanoic acid, less than about 25% by weight (S)-3-(Aminomethyl)-5-methylhexanoic acid and greater than about 75% by weight (R)-3-(Aminomethyl)-5-methylhexanoic acid, less than about 10% by weight (S)-(Aminomethyl)-5-methylhexanoic acid and greater than about 90% by weight (R)-3-(Aminomethyl)-5-methylhexanoic acid, less than about 1% by weight (S)-3-(Aminomethyl)-5-methylhexanoic acid and greater than about 99% by weight (R)-3-(Aminomethyl)-5-methylhexanoic acid, greater than about 50% by weight (S)-3-(Aminomethyl)-5-methylhexanoic acid and less than about 50% by weight (R)-3-(Aminomethyl)-5-methylhexanoic acid, greater than about 75% by weight (S)-3-(Aminomethyl)-5-methylhexanoic acid and less than about 25% by weight (R)-3-(Aminomethyl)-5-methylhexanoic acid, greater than about 90% by weight (S)-3-(Aminomethyl)-5-methylhexanoic acid and less than about 10% by weight (R)-3-(Aminomethyl)-5-methylhexanoic acid, or greater than about 99% by weight (S)-3-(Aminomethyl)-5-methylhexanoic acid and less than about 1% by weight (R)-3-(Aminomethyl)-5-methylhexanoic acid.

In a still further embodiment, the primary amine compound can consist essentially of or consist of (S)-3-(Aminomethyl)-5-methylhexanoic acid. In yet another embodiment, the primary amine compound can consist essentially of or consist of (R)-3-(Aminomethyl)-5-methylhexanoic acid.

In some embodiments, the primary amine compound is a compound having the following structural formula:

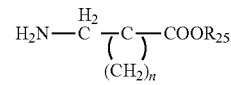

wherein $R_{25}$ is hydrogen or a lower alkyl, such as a ($C_1$-$C_6$) straight chain or branched unsubstituted or substituted alkyl, n is 4, 5, or 6 and pharmaceutically acceptable salts thereof. Compounds having the above noted structural formula and methods of forming such compounds are described in U.S. Pat. No. 4,024,175, which is incorporated by reference in its entirety.

Other examples of primary amine compounds that can be administered in combination with the agent are selected from the group consisting of: 5-amino-2,3-dihydrophthalazine-1,4-dione, 3,4-diethoxyaniline, 1-isopropyl-2-methylbenzimidazol-5-amine, N2-(4-dimethylaminophenyl)-1,3-benzothiazole-2,6-diamine, N-[(3-aminophenyl)methyl]-6-methoxy-chroman-4-amine, 1-[[4-(aminomethyl)phenyl]methyl]hexahydropyrimidin-2-one, 1-(2,4-diphenylpyrimidin-5-yl)ethanamine, 3-(5-aminopentyl)-1-[(E)-(5-nitro-2-furyl)methyleneamino]imidazolidine-2,4-dione, 2-amino-N-[1-[[1-[(2-amino-1-benzyl-2-oxo-ethyl)carbamoyl]-2-methyl-propyl]carbamoyl]-3-methyl-butyl]-4-methyl-pentanamide, 2-(2-furyl)bicyclo[2.2.1]hept-5-en-3-amine, 5-(3-aminophenyl)furan-2-carboxamidine, 3-(3-aminopropanoyl)-1-[(E)-[5-(4-methoxyphenyl)-2-furyl]methyleneamino]imidazolidine-2,4-dione, 4-amino-N-(2-amino-2-oxo-ethyl)benzamide, 4-amino-N-[2-oxo-2-[(2-oxooxazolidin-3-yl)amino]ethyl]benzamide, (1S,2S,4R)-2-amino-4-isopropenyl-1-methyl-cyclohexanol, 2-amino-4-benzyl-phenol, (3S,5R,8R,9S,10S,13R,14S)-14-amino-3-hydroxy-10,13-dimethyl-1,2,3,4,5,6,7,8,9,11,12,15,16,17-tetradecahydrocyclopenta[a]phenanthrene-17-carboxylic acid, methyl (3S,5R,8R,9S,10S,13R,14S)-14-amino-3-[(2S,5R)-5-hydroxy-6-methyl-tetrahydropyran-2-yl]oxy-10,13-dimethyl-1,2,3,4,5,6,7,8,9,11,12,15,16,17-tetradecahydrocyclopenta[a]phenanthrene-17-carboxylate, 1-[(E)-[5-(4-aminophenyl)-2-furyl]methyleneamino]-3-[4-(4-methylpiperazin-1-yl)butyl]imidazolidine-2,4-dione, 4-amino-2-hydroxy-benzoic acid, fluoranthen-3-amine, phenazine-2,3-diamine, 3-chloro-4-(4-chlorophenoxy)aniline, 4-(6-methyl-1,3-benzothiazol-2-yl)aniline, 3-[5-(1H-benzimidazol-2-yl)-2-furyl]aniline, N-(2-aminoethyl)-7-tert-butyl-3,3-dimethyl-2H-benzofuran-5-carboxamide, N'-benzylpropane-1,3-diamine, 5,6-dihydro-2-methyl-4H-pyrrolo[3,2,1-ij]quinoline-1-propanamine, 5-(4-aminophenyl)-2-(o-tolyl)pyrazol-3-amine, (2,3-dimethyl-1H-indol-5-yl)methanamine, 2,4-dimethyl-6-nitro-aniline, methyl 2-amino-4,5-dimethoxy-benzoate, 2-(5-propyl-1H-indol-3-yl)ethanamine, 2-(7-methoxy-5-nitro-1H-indol-3-yl)ethanamine, 5-amino-2-[(4-carboxyphenyl)carbamoyl]benzoic acid, 5-amino-2-[(3-carboxyphenyl)carbamoyl]benzoic acid, [2-[2-(3-aminobenzoyl)oxyphenyl]phenyl] 3-aminobenzoate, [4-[1-[4-(4-aminobenzoyl)oxyphenyl]-1-methyl-ethyl]phenyl] 4-aminobenzoate, 4-amino-N'-(4-chlorobenzoyl)benzohydrazide, 3-(4-aminophenyl)propanoic acid, 2,1,3-benzothiadiazole-4,5-diamine, 1H-benzimidazol-2-yl-methanamine, 2-amino-1-[16-(2-aminoacetyl)-1,4,10,13-tetraoxa-7,16-diazacyclooctadec-7-yl]ethanone, methyl 6-(2-aminophenyl)-6-oxo-hexanoate, 2-(3-amino-4-ethyl-phenyl)pyridin-3-ol, (5-amino-6,7-dimethoxy-3-methyl-benzofuran-2-yl)-morpholino-methanone, (3,5-diaminophenyl)methyl N-butylcarbamate, (3,5-diaminophenyl)methyl N-(2,4-dimethoxyphenyl)carbamate, 1-(4-aminophenyl)-3-(3,4-difluorophenyl)-1-phenyl-propan-2-one, N-(2-amino-ethyl)-2-[bis(2-hydroxyethyl)amino]acetamide, (Z)—N-(2-aminoethyl)-3-(1-naphthyl)prop-2-enamide, N-(2-aminoethyl)naphthalene-1-carboxamide, (2-amino-5-chloro-phenyl)-phenyl-methanone, 4-(4-bromophenoxy)aniline, 3-aminophenazin-2-ol, 5-amino-N-butyl-2-hydroxy-benzenesulfonamide, ethyl 2-[(2-aminophenyl)carbamothioylamino]acetate, 2-(2-aminophenyl)sulfanyl-4,6-dimethyl-pyridine-3-carbonitrile, 2-amino-1-phenyl-ethanone, 2-(2-methylphenoxy)aniline, (2-amino-5-chloro-phenyl)-(2-chlorophenyl)methanone, (1-phenylcyclopentyl)methanamine, tetralin-5-amine, 2-amino-3-(2-hydroxyphenyl)propanoic acid, 3-aminopropane-1-sulfinic acid, (3R,4R,5R)-2-[(1S,2S)-4,6-diamino-3-[(2R,3R)-3-amino-6-[1-(methylamino)ethyl]tetrahydropyran-2-yl]oxy-2-hydroxy-cyclohexoxy]-5-methyl-4-(methylamino)tetrahydropyran-3,5-diol, 4-ethoxyaniline, N-(4-amino-5-chloro-2-hydroxy-phenyl)benzenesulfonamide, 3-amino-N-(3,5-dichloro-2-hydroxy-4-methyl-phenyl)benzamide, 5,6,7,8-tetrahydrophenanthren-2-amine, 2-amino-N-(2-amino-1-benzyl-2-oxo-ethyl)-3-methyl-pentanamide, 1-benzylpiperidin-4-amine, (2R)-2-amino-3-ethylsulfanyl-propanoic acid, 2-amino-N-[2-(2,5-dioxopiperazin-1-yl)-2-oxo-ethyl]propanamide, 2-amino-3-(1H-imidazol-4-yl)propanamide, 2-amino-N-(2-naphthyl)acetamide, (2-amino-6-methyl-phenyl)-phenyl-methanone, 3-[2-(2-aminoethylamino)ethylamino]propanenitrile, 2-amino-1-(3-bromophenyl)ethanone, (1,1-dioxothiolan-3-yl)methanamine, 2,4,6-tritert-butylaniline, N1,N4-bis(4-amino-2-chloro-phenyl)terephthalamide, 4-[(3,4-diaminophenyl)methyl]benzene-1,2-diamine, 5-methoxy-2-methyl-1,3-benzothiazol-6-amine, 2-(2-methyl-5-nitro-imidazol-1-yl)ethanamine, 1-bromonaphthalen-2-amine, 4-amino-2,6-dibromo-benzenesulfonamide, N'-[(E)-(2-aminophenyl)methyleneamino]-N-(4-chloro-3-nitro-phenyl)oxamide, 2-bromo-4,5-dimethyl-aniline, ethyl 2-[(4-amino-3-nitro-benzoyl)amino]-4,5,6,7-tetrahydrobenzothiophene-3-carboxylate, 4-amino-2-morpholinosulfonyl-phenol, 4-[(4-amino-3,5-diethyl-phenyl)methyl]-2,6-diethyl-aniline, 5-[1-(3-amino-4-methyl-phenyl)-2,2,2-trifluoro-1-(trifluoromethyl)ethyl]-2-methyl-aniline, 4-pyridylmethanamine, 2-phenylbenzotriazole-4,5-diamine, 5-amino-2-hydroxy-N,N-dimethyl-benzenesulfonamide, methyl 2-amino-3-phenyl-propanoate, 4-amino-N-[4-[6-[(4-aminobenzoyl)amino]-7-chloro-1H-benzimidazol-2-yl]phenyl]benzamide, 3-chloro-4-(2-naphthyloxy)aniline, 2-bromo-6-(difluoromethylsulfonyl)-4-nitro-aniline, 5-(4-aminophenoxy)-2-(1-naphthyl)isoindoline-1,3-dione, 5-(3-aminophenoxy)-2-(1-naphthyl)isoindoline-1,3-dione, 7-[3-(aminomethyl)-1-piperidyl]-1-cyclopropyl-8-methoxy-4-oxo-quinoline-3-carboxylic acid, 7-[3-(1-amino-1-methyl-ethyl)-1-piperidyl]-1-cyclopropyl-8-methoxy-4-oxo-quinoline-3-carboxylic acid, N-(3-amino-4-chloro-phenyl)-4,4-dimethyl-3-oxo-pentanamide, (4-aminophenyl)-(4-fluorophenyl)methanone, 2-(5-fluoro-1H-indol-3-yl)ethanamine, N1-(4-methoxyphenyl)benzene-1,4-diamine, 2-nitro-5-piperazin-1-yl-aniline, 5-(4-methylpiperazin-1-yl)-2-nitro-aniline, 2-amino-N—[(Z)-1-(4-chlorophenyl)ethylideneamino]benzamide, 3-amino-N-(2-amino-5-methyl-phenyl)-N-benzyl-benzamide, 1-[(Z)-1-(4-aminophenyl)ethylideneamino]-3-(m-tolyl)thiourea, 2-amino-4-cyclopropyl-6-(4-methoxyphenyl)benzene-1,3-dicarbonitrile, 2-(2-naphthyl)-1,3-benzoxazol-5-amine, N-[(E)-1-(4-aminophenyl)ethylideneamino]furan-2-carboxamide, 4-(4-aminophenyl)thiazol-2-amine, (2R)-2-acetamido-6-[[(2R)-2-aminobutanoyl]amino]-N-[[3-(trifluoromethyl)phenyl]methyl]hexanamide, (4S)-5-[[(5R)-5-acetamido-6-oxo-6-(propylamino)hexyl]amino]-4-amino-5-oxo-pentanoic acid, N-[(1R)-5-[[4-(aminomethyl)cyclohexanecarbonyl]amino]-1-[[(2R)-2-hydroxypropyl]carbamoyl]pentyl]thiophene-2-carboxamide, N-[(1R)-1-(allylcarbamoyl)-5-[(4-aminobenzoyl)amino]pentyl]thiophene-2-carboxamide, (4S)-4-amino-5-oxo-5-[[(5R)-6-oxo-6-[2-(2-thienyl)ethylamino]-5-(thiophene-2-carbonylamino)hexyl]amino]pentanoic acid, 2-[(6-amino-1,3-benzothiazol-2-yl)sulfanyl]-N-(2-fluorophenyl)acetamide, N-(5-amino-2-methoxy-phenyl)-2,4-dichloro-benzamide, N-(6-amino-4-methyl-1,3-benzothiazol-2-yl)acetamide, 3-amino-N'-[2-(2-naphthyloxy)acetyl]-5-nitro-benzohydrazide, 2-(2-aminophenyl)sulfanyl-N-[3,5-bis(trifluoromethyl)phenyl]-2-phenyl-acetamide, ethyl 2-[[2-[2-[[2-amino-3-(4-hydroxyphenyl)propanoyl]amino]propanoylamino]acetyl]amino]acetate, 2-amino-5-chloro-N-(4-pyridylmethyl)benzamide, 8-nitronaphthalen-1-amine, 2-amino-3-cyclopropyl-propanoic acid, 2-(2-isopropyl-5-methyl-phenoxy)ethanamine, 2-amino-N-[(E)-1-(2-hydroxyphenyl)ethylideneamino]benzamide, (2R)-2-amino-3-benzhydrylsulfanyl-propanoic acid, tert-butyl 2-aminopropanoate, 2-[4-(1-ethylpropyl)phenoxy]-5-(trifluoromethyl)aniline, N1-methylbenzene-1,3-diamine, 1-(4-aminophenyl)sulfanyl-3-(diethylamino)propan-2-ol, N-(4-aminophenyl)-2,2-dimethyl-propanamide, 2-amino-3-(4-nitrophenyl)butanoic acid, 2-(2-amino-5-bromo-phenyl)-4-methyl-benzo[g]quinoxalin-3-one, N-[3-[(2-aminophenyl)methylamino]-1-methyl-3-oxo-propyl]-2-phenyl-quinoline-4-carboxamide, N-[2-[(2-aminophenyl)methylamino]-2-oxo-1-phenyl-ethyl]-2-phenyl-quinoline-4-carboxamide, (5S)-5-(4-aminobutyl)-3-[4-(o-tolyl)phenyl]imidazolidine-2,4-dione, (5S)-5-(4-aminobutyl)-3-[4-(benzothiophen-2-yl)-1-naphthyl]-2-thioxo-imidazolidin-4-one, 2-amino-4,6-ditert-butyl-phenol, 5-(aminomethyl)-2,4-dimethyl-pyridin-3-amine, 3-amino-N-[5-hydroxy-1-(2,4,6-trichlorophenyl)pyrazol-3-yl]benzamide, (2R)-2-amino-3-(4-fluorophenyl)-N-[4-guanidino-1-(1-piperidylmethyl)butyl]propanamide, 3-[[2-[2-(3-aminopropylcarbamoyl)phenyl]benzoyl]-[(2,5-difluorophenyl)methyl]amino-]propanoic acid, N-[(4-acetamidophenyl)methyl]-N-(3-amino-2,2-dimethyl-propyl)-2-(4-ethylphenyl)pyridine-4-carboxamide, N-(3-aminopropyl)-2-(4-ethylphenyl)-N-[(3,4,5- trimethoxyphenyl)methyl]pyridine-4-carboxamide, N-(2-aminoethyl)-5-(4-fluorophenyl)-N-(2-pyridylmethyl) pyridine-3-carboxamide, N-[[4-(aminomethyl)phenyl]methyl]-5-(1-naphthyl)-N-(2-pyridylmethyl)pyridine-3-carboxamide, 2-(3-acetylphenyl)-N-(3-aminopropyl)-N-(2,3-dihydro-1,4-benzodioxin-6-ylmethyl)pyridine-4-carboxamide, 2-[(4S,5R)-2-[(1R)-1-amino-2-(4-fluorophenyl)ethyl]-5-(2-naphthyl)tetrahydropyran-4-yl] acetonitrile, (2R)-2-amino-1-[(2S,4R)-4-benzyloxy-2-[2-(1,2,4-triazol-4-yl)ethyl]pyrrolidin-1-yl]-3-(4-fluorophenyl) propan-1-one, (2R)-2-amino-3-phenyl-1-[4-phenyl-4-(1,2,4-triazol-1-ylmethyl)-1-piperidyl]propan-1-one, N'-cyclododecylethane-1,2-diamine, 7-[2-[(2-amino-2-methyl-propyl)amino]pyrimidin-4-yl]-6-(4-fluorophenyl)-2,3-dihydro-1H-pyrazolo[1,2-a]pyrazol-5-one, 2,3,4,5-tetrahydro-1-benzothiepin-5-amine, 5-[(2R,3R,4S)-3-amino-4-(methoxycarbonylamino)tetrahydrothiophen-2-yl] pentanoic acid, 3-(2-aminophenyl)sulfanyl-3-(3,4-dichlorophenyl)-1-phenyl-propan-1-one, and pharmaceutically acceptable salts thereof.

In still other embodiments, the primary amine compound can be retinylamine and/or a retinylamine derivative, such as described in PCT/US2015/033585, filed Jun. 1, 2015.

In some embodiments, the retinylamine derivative can be a retinylamine peptide derivative that has the following formula:

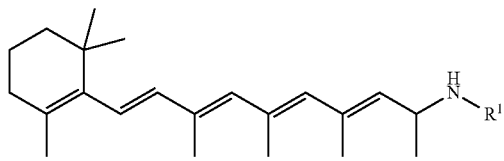

where $R^1$ is a peptide or oligopeptide that improves intestinal adsorption and targeting of the retinylamine peptide derivative to the retina of a subject upon enteral administration of the composition to the subject. For example, $R^1$ can be selected from the group consisting of L-phenylalanine, L-leucine, L-isoleucine, L-alanine, L-proline, L-valine, glycine, β-alanine, D-alanine, D-valine, glycine-glycine, L-valine-glycine, and glycine-L-valine.

The agents used in methods described herein can be administered to the subject to treat the diabetic retinopathy using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day.

The treatment methods can include administering to the subject a therapeutically effective amount of the agents alone or in combination. Determination of a therapeutically effective amount is within the capability of those skilled in the art. The exact formulation, route of administration, and dosage can be chosen by the individual physician in view of the subject's condition.

In some embodiments, a combination of agents described herein can be administered to a subject as a combination therapy to treat diabetic retinopathy in a subject or reduce the risk of diabetic retinopathy in the subject. The phrase "combinatorial therapy" or "combination therapy" embraces the administration of one or more agents described herein, and/or potentially one or more other therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

For example, a therapeutically effective amount at least two or more, three or more, or four or more of a primary amine, retinylamine, retinylamine derivative, retinoid derivative, Gs coupled receptor antagonist (e.g., serotonin receptor antagonist), a Gq coupled receptor antagonist (e.g., alpha-1 receptor antagonist), a Gi coupled receptor agonist (alpha-2 adrenergic receptor agonist), an adenylyl cyclase inhibitor, NADPH oxidase inhibitor, or a PLC inhibitor can be administered to a subject to treat the diabetic retinopathy. In still other examples, a combination of agents that is administered to a subject to treat an diabetic retinopathy can include: at least two or more of a primary amine, retinylamine, retinylamine derivative, Gs coupled receptor antagonist (e.g., serotonin receptor antagonist), a Gq coupled receptor antagonist (e.g., alpha-1 receptor antagonist), a Gi coupled receptor agonist (alpha-2 adrenergic receptor agonist), NADPH oxidase inhibitor, or an adenylyl cyclase inhibitor, but not a PLC inhibitor; at least two or more of at least two or more of a primary amine, retinylamine, retinylamine derivative, Gs coupled receptor antagonist (e.g., serotonin receptor antagonist), a Gq coupled receptor antagonist (e.g., alpha-1 receptor antagonist), a Gi coupled receptor agonist (alpha-2 adrenergic receptor agonist), NADPH oxidase inhibitor, or PLC inhibitor, but not an adenylyl cyclase inhibitor; at least two or more of a primary amine, retinylamine, retinylamine derivative, Gs coupled receptor antagonist (e.g., serotonin receptor antagonist), a Gq coupled receptor antagonist (e.g., alpha-1 receptor antagonist), adenylyl cyclase inhibitor, NADPH oxidase inhibitor, or PLC inhibitor, but not an a Gi coupled receptor agonist (alpha-2 adrenergic receptor agonist); at least two or more of a primary amine, retinylamine, retinylamine derivative, Gs coupled receptor antagonist (e.g., serotonin receptor antagonist), Gi coupled receptor agonist (alpha-2 adrenergic receptor agonist), adenylyl cyclase inhibitor, NADPH oxidase inhibitor, or PLC inhibitor, but not a Gq coupled receptor antagonist (e.g., alpha-1 receptor antagonist); or at least two or more of a primary amine, retinylamine, retinylamine derivative, Gq coupled receptor antagonist (e.g., alpha-1 receptor antagonist) Gs Gi coupled receptor agonist (alpha-2 adrenergic receptor agonist), adenylyl cyclase inhibitor, NADPH oxidase inhibitor, or PLC inhibitor, but not a Gs coupled receptor antagonist (e.g., serotonin receptor antagonist).

The dose, amount, and/or quantity of the agents described herein which are administered to the subject can depend on the specific primary amine, retinylamine, retinylamine derivative, retinoid derivative, Gs coupled receptor antagonist (e.g., serotonin receptor antagonist), Gq coupled receptor antagonist (e.g., alpha-1 receptor antagonist), Gi coupled receptor agonist (alpha-2 adrenergic receptor agonist), adenylyl cyclase inhibitor, NADPH oxidase inhibitor and/or PLC inhibitor selected. It will be appreciated that the dosage amounts used will depend on the potency of the specific primary amine, retinylamine, retinylamine derivative, retinoid derivative, Gs coupled receptor antagonist (e.g., serotonin receptor antagonist), Gq coupled receptor antagonist (e.g., alpha-1 receptor antagonist), Gi coupled receptor agonist (alpha-2 adrenergic receptor agonist), adenylyl cyclase inhibitor, NADPH oxidase inhibitor and/or PLC inhibitor and the therapeutic regimen employed.

In another aspect embodiment, the specific primary amine, retinylamine, retinylamine derivative, retinoid derivative, Gs coupled receptor antagonist (e.g., serotonin receptor antagonist), Gq coupled receptor antagonist (e.g., alpha-1 receptor antagonist), Gi coupled receptor agonist (alpha-2 adrenergic receptor agonist), adenylyl cyclase inhibitor, NADPH oxidase inhibitor and/or PLC inhibitor when administered in combination to subject can be administered at an amount or dosage to achieve a therapeutic effect that is substantially less (i.e., subtherapeutic dose or amount) than the amount or dose that would be required to achieve a therapeutic effect if each compound was administered alone. Co-administration of specific primary amine, retinylamine, retinylamine derivative, retinoid derivative, Gs coupled receptor antagonist (e.g., serotonin receptor antagonist), Gq coupled receptor antagonist (e.g., alpha-1 receptor antagonist), Gi coupled receptor agonist (alpha-2 adrenergic receptor agonist), adenylyl cyclase inhibitor, NADPH oxidase inhibitor, and/or PLC inhibitor to the subject can also mitigate resistance to one single agent. Such resistance results either in the requirement for higher dosages of the drug and/or the renewed symptoms.

Moreover, co-administration of specific primary amine, retinylamine, retinylamine derivative, retinoid derivative, Gs coupled receptor antagonist (e.g., serotonin receptor antagonist), Gq coupled receptor antagonist (e.g., alpha-1 receptor antagonist), Gi coupled receptor agonist (alpha-2 adrenergic receptor agonist), adenylyl cyclase inhibitor, NADPH oxidase inhibitor, and/or PLC inhibitor to the subject can mitigate toxicity and side effects associated with potentially administering a single agent at an amount effective to achieve a therapeutic effect. If two or more agents are used in concert, the dosage of any single drug can be lowered. This is beneficial to the patient since using lower levels of therapeutic agents is generally safer for the patient. Additionally, cells are less likely to generate resistance to the combination of drugs as they are to a single drug. Thus in some aspects, the agents described herein can be administered to a subject at a subtherapeutic level.

Formulation of pharmaceutical compositions using agents described herein for use in the modes of administration noted above (and others) are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, one or more of the agents can be provided in an ophthalmic preparation that can be administered to the subject's eye. The ophthalmic preparation can contain the agent in a pharmaceutically acceptable solution, suspension or ointment. Some variations in concentration will necessarily occur, depending on the particular agent employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The agents can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin can include, for example, ointments, creams, gels and pastes comprising the agent in a pharmaceutical acceptable carrier. The formulation of the agent for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with or at risk of diabetic retinopathy, which are not readily accessible or suitable for ophthalmic (e.g. eye-drops) and/or topical administration, can be treated by a systemic approach, such as intravenous infusion. For example, the agent can be administered at a low dosage by continuous intravenous infusion. In another example, in which a patient requires longer-term care, the agent can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the agent to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the agent.

In one embodiment, a subject is diagnosed as having symptoms of diabetic retinopathy, and then a disclosed compound is administered. In another embodiment, a subject may be identified as being at risk for developing diabetic retinopathy (risk factors include a history of smoking, age, female gender, and family history), and then a disclosed compound is administered. In another embodiment, a subject may have diabetic retinopathy, and then a disclosed compound is administered. In some embodiments, a compound is administered prophylactically. In some embodiments, a subject has been diagnosed as having the disease before retinal damage is apparent. In some embodiments, a human subject may know that he or she is in need of the diabetic retinopathy treatment or prevention.

In some embodiments, a subject may be monitored for the extent of retinal degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing diabetic retinopathy or other forms of retinal disease. For example, a patient may be treated with more than one therapy for one or more diseases or disorders.

The invention is further illustrated by the following examples, which are not intended to limit the scope of the claims.

Example 1

In this Example, we demonstrate that administration of Ret-NH$_2$ to diabetic animals inhibits both the vascular (capillary degeneration and abnormal leakage) and neural (visual function) defects that characterize early stages of DR. In addition, the unique actions of Ret-NH$_2$ provide unique insight into the pathogenesis of DR. Our findings suggest that RPE cells and possibly also the visual cycle contribute to the development of DR. Neither the RPE nor enzymes of the visual cycle have previously been identified as potential contributors to the pathogenesis of DR or as targets for therapeutic inhibition of that retinopathy.

Experimental Procedures

Experimental Animals

Male C57Bl/6J mice, Lrat$^{-/-}$ mice, and mice in which the P23H mutation of rhodopsin was knocked in were randomly assigned to become diabetic or remain nondiabetic. Diabetes was induced by 5 sequential daily intraperitoneal injections of a freshly prepared solution of streptozotocin in citrate buffer (pH 4.5) at 60 mg/kg of body weight. After hyperglycemia was verified at least 3 times during the second week after streptozotocin, diabetic mice were randomly assigned to remain as untreated diabetic controls or to be administered therapy. Insulin was given as needed to prevent weight loss without preventing hyperglycemia and glucosuria (0-0.2 units of NPH insulin subcutaneously, 0-3 times per week). Blood glucose and HbA1c were measured as reported previously. Since blood sugar and insulin treatment are known to influence the development and severity of the retinopathy, considerable effort was made to keep glycemia similar in diabetics treated with and without Ret-NH$_2$. Treatment of animals conformed to the ARVO Resolution on Treatment of Animals in Research, as well as to institutional guidelines. Animals were studied for 2 months or 8 months durations of diabetes in order to investigate effects of potential therapies on molecular and histopathologic changes of the retina, respectively. All animals were killed 4-6 days after the last injection of Ret-NH$_2$.

Ret-NH$_2$ was synthesized. Initially, a single dose of the amine was injected intraperitoneally into diabetic mice at doses of 0.05-1.0 mg/mouse, and retinal generation of superoxide and visual function were measured 3, 7 and 14 days later. Several diabetic mice died after administration of the 1 mg/mouse dose, so that dose was not studied further. Then, the selected lower dose was administered once per week to diabetic mice for 2 months, while assessing effects of the therapy on retinal superoxide, expression of inflammatory proteins, and visual function. After selection of a safe and effective dose and frequency of its administration (0.2 mg/animal once per week), a long-term (8 months) study was performed to assess the effects of this treatment on diabetes induced degeneration and dysfunction of retinal capillaries and visual function. Retinylamine not given to nondiabetic animals.

Leakage of Albumin into Neural Retina

Accumulation of the blood protein, albumin, in the neural retina has been viewed as a marker of increased vascular permeability. At 8 months of diabetes, sterile FITC-BSA (50 µg/µl) in phosphate buffered saline (NaCl, 0.138 M; KCl, 0.0027 M; pH 7.4) was injected into the tail vein of mice at 100 µg/g. After 20 min, mice were euthanized, and their eyes were fixed in ice-cold 4% paraformaldehyde and then frozen in O.C.T. (Optimal cutting temperature compound) in isopentane on dry ice after infusion with sucrose. Retinal cryosections were cut and viewed by fluorescence microscopy. Leakage of albumin was estimated from measurements of FITC-BSA in the inner nuclear layer (I.N.L) of the neural retina using computer-assisted microscopy. Vascular permeability in diabetes is expressed as the ratio of FITC-dextran concentration in neural retina relative to that in plasma and compared to that of nondiabetic animals.

Diabetes-Induced Retinal Histopathology

DR is a slowly developing disease, and rodent models develop only the early stages of the retinopathy during their life. After 8 months of diabetes, mouse eyes were fixed in formalin, and one retina from each animal was isolated, washed in running water overnight, and digested for 2 h in elastase as we previously reported. When totally cleaned of neural cells, the isolated vasculature was laid out on a glass microscope slide, dried overnight, stained with hematoxylin and periodic acid-Schiff, dehydrated and coverslipped. Degenerate (acellular) capillaries were quantitated in 6-7 field areas corresponding to the mid-retina (200× magnification) in a masked manner. Acellular capillaries reported per square millimeter of retinal area were identified as capillary-sized vessel tubes having no nuclei along their length.

We assessed whether or not photoreceptors had degenerated in diabetic mice by counting the number of layers in the outer nuclear layer (ONL) in histologic cross-sections of retina. Using photomicrographs generated for the permeability measurements, we counted the number of cells of the ONL in 2 areas on either side of the optic nerve (~300 μm from the optic nerve), and the resulting values were averaged together to compute a single estimate for each animal. WT diabetic and nondiabetic mice from the 8-month study served as controls also for another experiment run at the same time; data from these control experiments are provided here for the convenience of readers.

Western Blots

Retinas were isolated, sonicated and centrifuged, and the supernatants were used for western blots. Samples (50 μg) were fractionated by SDS-PAGE, electroblotted onto nitrocellulose membranes, and membranes were blocked in Tris buffered saline containing 0.02% Tween 20 and 5% nonfat milk. Antibodies for ICAM-1 (1:2000; Proteintech, Chicago, Ill.) and iNOS (1:1000 dilution; Santa Cruz Biotechnology, Santa Cruz, Calif.), p-IκB and IκB (1:200 and 1:1000 dilutions, respectively; both from Santa Cruz Biotechnology, Santa Cruz, Calif.) were applied, followed by secondary antibody for 1 h. After washing, slides were visualized for enhanced chemiluminescence.

Measurement of Visual Cycle Intermediates

Eyes from WT control and mice diabetic for 2 months were collected after 24 h dark adaptation. For retinoid extraction and HPLC analyses, all procedures were carried out under dim red light. Retinoids were extracted from eyecups including the retina and RPE. The tissue was transferred into 200 μl of 2 M $NH_2OH$ (pH 6.8) and 200 μl of methanol and homogenized by sonication (5 bursts for 5 s, 20% of maximum power). Retinoids were extracted from the homogenate as described previously. HPLC analysis was performed on a normal phase ZORBAX Sil column (Agilent Technologies) in 10% ethyl acetate/hexane at an isocratic flow rate of 1.4 ml/min. Individual retinoids were determined by their retention times and spectral characteristics as compared with those of authentic standards. For quantification of molar amounts, peak integrals were scaled with defined amounts of reference retinoids. The reference retinoids all-trans-retinyl palmitate, 11-cis-retinal, and all-trans-retinal were purchased from Toronto Research Chemicals (Toronto, Canada). Corresponding retinal oximes were obtained by their reaction with $NH_2OH$. The amount of a retinal isomer was determined by the total peak areas of both its syn- and anti-retinal oxime. Resulting amounts were summed to provide the total amount of 11-cis-retinal and all-trans-retinal in pmol per eye.

LRAT Activity Assay

Homogenates were made from both leukocytes from WT and $Lrat^{-/-}$ mice, and from immortalized mouse retinal endothelial cells. The reaction of all-trans-retinol esterification was carried out essentially. Mouse leukocytes or retinal endothelial cells lysates (~50 mg of protein) were incubated in 10 mM Tris/HCl buffer, pH 7.5, 1% bovine serum albumin with all-trans-retinol delivered in 1 μl of N,Ndimethylformamide to a final concentration of 10 μM. The total volume of the reaction mixture was fixed at 200 μl. Reactions were incubated at 30° C. for 1 h and then stopped by adding 300 μl of methanol followed by the same volume of hexane. Retinoids were extracted and analyzed by chromatographic method described above in a stepped gradient of ethyl acetate in hexane (1% from 0 to 10 min, 10% up to 30 min, at the flow rate of 1.4 ml/min).

Optokinetic Assessment of Photopic Visual Function

The spatial frequency threshold, a marker of visual acuity, and contrast sensitivity threshold were measured with the Virtual Optokinetic system. The maximum spatial frequency capable of driving head tracking was determined as the spatial frequency threshold. The contrast sensitivity at 8 months of study was measured at 6 spatial frequencies to detect functional defects in spatially sensitive retinal cells or in higher visual pathways. This was determined as the inverse of Michelson contrast without correction for luminance of the monitors. At 2 months of study, only a single spatial frequency (0.064 c/d) was measured to estimate contrast sensitivity. The experimenter was masked as to the identity of the experimental group.

Retinal Explants

Eyes were enucleated from adult C57Bl/6J mice and immediately immersed in ice-cold DMEM containing 10% FBS, penicillin (100 U/ml) and streptomycin (100 μg/ml). The posterior pole (including the retina) was incubated for 3 days in DMEM in a humidified incubator with 5% $CO_2$ at 37° C., keeping the retina in contact with the RPE. The culture medium was changed every other day. At the end of this incubation, the retina was separated from the RPE prior to the assay for superoxide described above.

Endothelial Co-Culture with Leukocytes

The retinal endothelial cells were grown in control medium (DMEM with 5 mM glucose) containing 10% serum. The serum concentration was reduced to 2% just before cells were placed either in 5 mM glucose or high glucose (30 mM). Media was changed every other day for 3 days. When cells reached 80% confluence (~300,000 cells), freshly isolated leukocytes from blood (100,000 cells) were added and incubated for 6 additional h, after which cells and media were collected and washed with PBS. Cells were stained with an antibody against CD144 to identify endothelial cells, and the viability of the endothelial cells was identified by flow cytometry based on 7-AAD staining. Cell death was expressed as the percentage of endothelial cells that stained with dyes. Approximately 10,000 cells were counted in each sample. Experiments were repeated two times with similar results each time.

Statistical Analyses

Data are expressed as means±SDs. All statistical analyses were performed with ANOVA followed by Fischer's test, except for the full contrast sensitivity curve which was analyzed by repeated measures ANOVA to account for testing each animal at multiple spatial frequencies. Values of $p<0.05$ were considered statistically significant.

Results

Glycemia was elevated in all diabetic animals, and administration of $Ret-NH_2$ once per week for the duration of this study did not alter this observation. Average glycated hemoglobin over the entire duration of the 8-month experiment was 3.4±0.2%, 11.1±0.6, and 10.8±0.7 for the non-diabetic, diabetic control, and diabetic treated with Ret-NH$_2$ groups, respectively, and average nonfasted blood glucose values for these groups over the 8 month study were 148 mg/dl±22, 528±52, and 482±66. Final body weights in these groups were 46±3 g, 29±2, and 29±3, respectively. Data from the 2-month experiment were similar. Chronic administration of Ret-NH$_2$ had no detectable effect on glycemia or health of the animals. Because a fraction of glucose exists as an aldehyde in vivo and Ret-NH$_2$ sequesters aldehydes, the possibility that Ret-NH$_2$ might lower blood glucose was considered. However, our data indicate that observed effects of Ret-NH$_2$ were not mediated by lowering blood glucose.

Dose-Ranging Study in Diabetic Mice

Our initial studies sought to determine the dose and frequency of Ret-NH$_2$ administration that would be efficacious in diabetes, using the diabetes-induced increase in retinal generation of superoxide as the endpoint. After a single injection of Ret-NH$_2$, all doses of the compound tested reduced the retinal production of superoxide in a dose-dependent manner (FIG. 1A), with the 0.5 mg/mouse dose totally normalizing superoxide generation for one week and other doses having a lesser effect. The highest dose, however, transiently impaired visual function (spatial frequency threshold; FIG. 1B), whereas the lower doses neither improved nor further impaired visual function. This dose-ranging study led to the selection of a once weekly administration of 0.2 mg/mouse of Ret-NH$_2$ for subsequent studies.

Inhibition of Diabetes-Induced Retinal Histopathology and Permeability by Ret-NH$_2$ Longterm (8 months) diabetes resulted in a significant ($p<0.0001$) increase in the number of degenerate (acellular) capillaries in the retina of control animals (FIG. 2A). Diabetes of 8 months also resulted in a significant ($p<0.01$) increase in the levels of albumin extravasation into the nonvascular retina (i.e., in the neural retina between vessels) in the inner plexiform layer (IPL) during the preceding 20 minutes (FIG. 2B). Weekly injection of Ret-NH$_2$ significantly reduced the diabetes-induced degeneration of retinal capillaries and albumin accumulation in the retina ($p<0.0001$ and $p<0.05$, respectively).

Visual Function

We also measured spatial frequency threshold and contrast sensitivity in diabetes, both being psychophysical measures that assess the function of retinal and central visual pathways. Diabetes of 2 and 8 months duration significantly ($p<0.01$) lowered the spatial frequency threshold, but Ret-NH$_2$ had no significant benefit on this defect (0.399 c/d±0.004, 0.357±0.007, and 0.366±0.007 for nondiabetic controls, diabetic controls and diabetics treated with RetNH$_2$ for 2 months, respectively, and 0.396±0.009, 0.359±0.007, and 0.364±0.009 for 8 months of study). Contrast sensitivity was measured at 6 spatial frequencies at 8 months of diabetes, and repeated measures analysis indicated that diabetes significantly inhibited the contrast sensitivity curve ($p<0.0001$), and Ret-NH$_2$ had a small (but significant; $p<0.05$) benefit on this defect.

Effect of Ret-NH$_2$ on Retinal Oxidative Stress and Inflammation

In an effort to investigate the mechanism by which Ret-NH$_2$ inhibited dysfunction and degeneration of retinal cells and capillaries in diabetes, we measured several parameters found in other studies to be causally related to diabetes induced retinopathy. Thus we focused initially on oxidative stress and inflammation.

Figure 3:
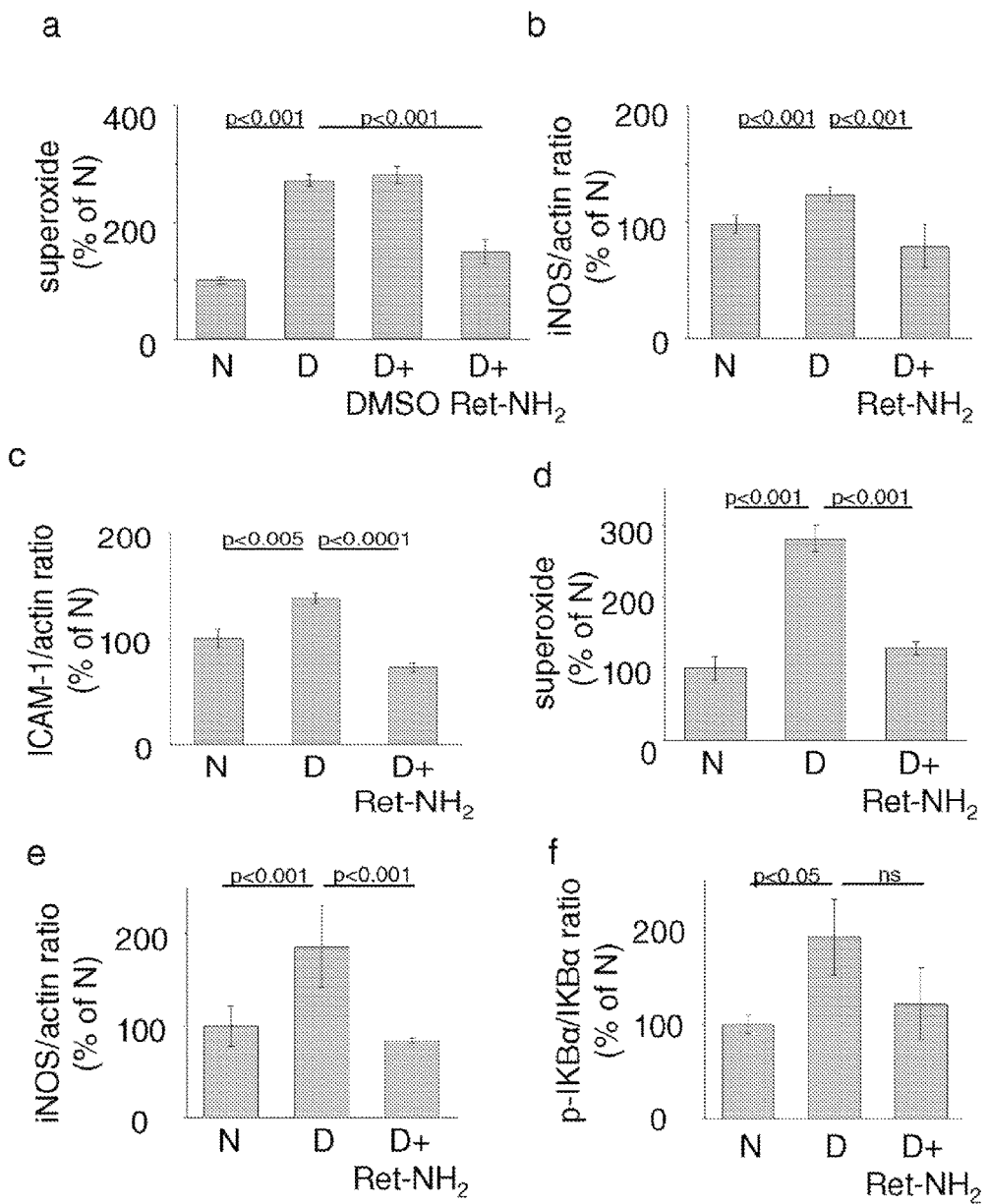
FIGS. 3(A-F) illustrate graphs showing the effect of Ret-NH$_2$ on diabetes-induced increases in retinal superoxide and expression of proinflammatory proteins at 2 (A-C) and 8 (D-F) months of diabetes. Panel a includes a DMSO control to demonstrate that this solvent had no effect on parameters measured. Diabetes was induced at 2 months of age. n=4-7 in all groups.

Diabetes significantly increased superoxide and inflammation (iNOS, ICAM-1, p-iKB as assessed by Western blot) in the retina at both 2 (FIGS. 3A-C) and 8 (FIGS. 3D-F) months duration of diabetes. Weekly administration of Ret-NH$_2$ for the entire duration of these studies markedly reduced the diabetes-induced increase in retinal superoxide and iNOS and ICAM-1 expression.

Because Ret-NH$_2$ is known to inhibit photoreceptor degeneration caused by accumulation of all-trans-retinal in retinal degeneration models, we considered the possibility that diabetes might cause photoreceptor loss, and that might be preventable by Ret-NH$_2$ therapy. In contrast to photoreceptor loss in retinal degeneration (and to the observed degeneration of retinal capillaries in the current study of diabetic mice), diabetes of 8 months duration did not produce a loss of photoreceptor cells compared to nondiabetic controls (12.6±0.8 layers of nuclei in ONL versus 11.2±0.7, respectively). Weekly treatment of diabetic mice with Ret-NH$_2$ had no significant effect on photoreceptor number (12.4±1.7; not significant compared to diabetic or nondiabetic WT controls). Moreover, diabetes of 2 months duration did not alter levels of 11-cis-retinal or all-trans-retinal in dark-adapted retinas (Table 1). Diabetes did however significantly increase levels of retinyl esters that contribute to 11-cis-retinal formation. Because diabetes did not cause photoreceptor degeneration or alterations in levels of all-trans-retinal in our study, we conclude that the observed beneficial effects of Ret-NH$_2$ were not mediated by prevention of these defects.

TABLE 1

Effect of 2 months diabetes on visual cycle intermediates in eyes from C57Bl/6J mice (pmol/eye)

| | Group | 11-cis-retinal | all-trans-retinal | Retinyl esters |
|---|---|---|---|---|
| Unbleached | N | 353 ± 24*1 | 54 ± 7 | 71 ± 5 |
| | D | 395 ± 32* | 47 ± 5 | 225 ± 57† |
| Bleached | N | 415 ± 40 | 53 ± 7 | 128 ± 15 |
| | D | 416 ± 11 | 40 ± 1* | 182 ± 52 |

Different from N at *p < 0.05 or †p < 0.001
1Mean ± SD

Figure 4:
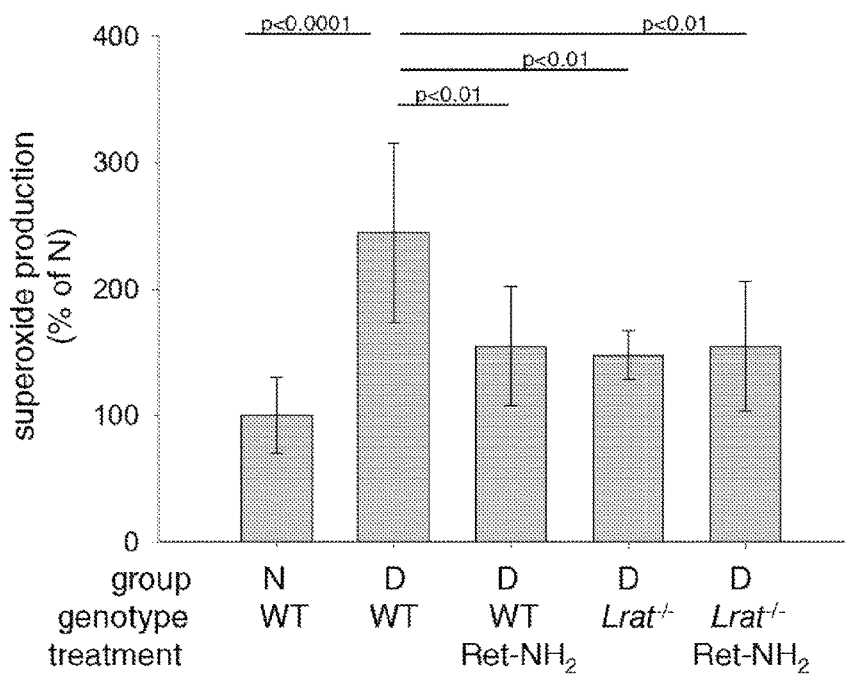
FIG. 4 illustrates a graph showing diabetes-induced increase in superoxide generation by mouse retina is inhibited by weekly treatment with Ret-NH$_2$ or by deficiency of LRAT. Ret-NH$_2$ given to Lrat$^{-/-}$ mice did not further inhibit retinal superoxide production. The duration of diabetes was 2 months, and all mice were 4 months of age. Ret-NH$_2$ was administered weekly from the onset of diabetes. n=5 in all groups.

LRAT catalyzes the formation of retinyl esters, which are storage forms of vitamin A. Ret-NH$_2$ is a derivative of vitamin A, and thus LRAT also amidates Ret-NH$_2$, thereby allowing it to be stored in those cells that contain LRAT. LRAT also participates in the visual cycle to regenerate 11-cis-retinal for continuing vision. To investigate if LRAT is required for the beneficial effects of Ret-NH$_2$, we studied Lrat-deficient diabetic mice. In retinas from WT controls diabetic for 2 months duration, the expected increase in retinal superoxide generation compared to controls was observed, and Ret-NH$_2$ administration (once per week) inhibited this increase (FIG. 4). Surprisingly, retinal superoxide generation was greatly inhibited also in diabetic mice deficient in LRAT. Thus, even in absence of Ret-NH$_2$, LRAT deficiency prevented the diabetes-induced increase in superoxide generation by the retina.

Figure 5:
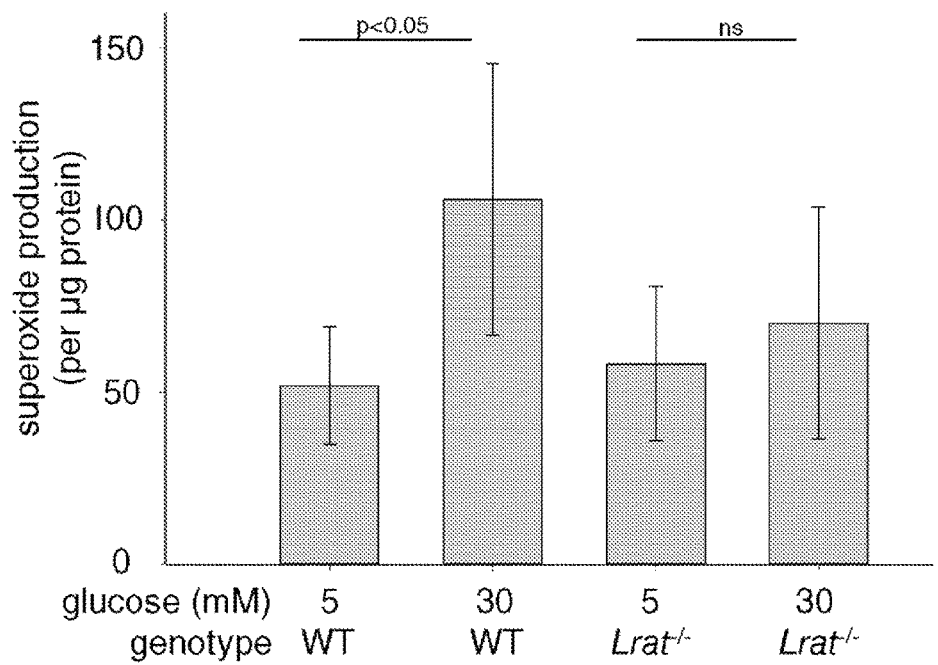
FIG. 5 illustrates a graph showing retinal explants involving posterior eyecups from WT or Lrat$^{-/-}$ mice reveal that superoxide generation in elevated glucose is derived from the retina, and is reduced by the absence of LRAT in the RPE. Eyecups were obtained from nondiabetic C57Bl/6J (WT) or Lrat$^{-/-}$ mice at age 2-3 months. The duration of incubation was 3 days, and media was changed after 2 days. n=5-6 in all groups.

To confirm the in vivo findings, posterior eyes from non-diabetic WT and Lrat$^{-/-}$ mice were organ cultured for 3 days in levels of glucose comparable to those seen in diabetic (30 mM) and nondiabetic (5 mM) patients, and then retinal superoxide measured. Retinal explants from WT mice in 30 mM glucose showed a significant increase in retinal superoxide generation compared to those incubated in 5 mM glucose, whereas retinas from Lrat$^{-/-}$ mice incubated in elevated glucose did not increase the generation of superoxide (FIG. 5).

We evaluated the number of nuclear layers in the ONL of 4-month-old WT and Lrat$^{-/-}$ mice to learn if photoreceptor degeneration could contribute to the absence of retinal oxidative stress in Lrat$^{-/-}$ mice. Our LRAT-deficient mice had 18% fewer nuclear layers in the ONL than did age-matched WT controls (8.9±0.3 and 10.8±2.8 nuclear layers adjacent to the optic nerve in Lrat$^{-/-}$ mice and WT mice, respectively). However it seems unlikely that the total inhibition of retinal superoxide generation in our Lrat$^{-/-}$ diabetic mice (FIG. 5) was due solely to this modest loss of photoreceptors compared to that in WT mice.

We have implicated leukocytes as contributing to the development of DR, and killing of retinal endothelial cells has been demonstrated with leukocytes from both diabetic patients and animals. We isolated the leukocyte fraction from the blood of animals in the various experimental groups, and assessed effects of in vivo Ret-NH$_2$ treatment on both basal superoxide generation by these leukocytes and leukocyte mediated killing of retinal endothelial cells. Weekly administration of Ret-NH$_2$ to diabetic animals significantly inhibited both of these diabetes-induced defects (FIG. 6).

To determine if the inhibition of leukocyte mediated cytotoxicity against endothelial cells by Ret-NH$_2$ was dependent on LRAT, we tested if LRAT activity is present in leukocytes and endothelial cells, and if LRAT deficiency in mice diabetic for 2 months altered leukocyte-mediated killing of retinal endothelial cells compared to that in WT diabetic animals. Measurement of LRAT enzymatic activity in freshly isolated leukocytes or the retinal endothelial cell line revealed a lack of LRAT activity in both cell types (FIG. 7). In studies to determine if LRAT deficiency altered the diabetes-induced leukocyte-mediated killing of retinal endothelial cells, we showed that leukocytes from Lrat$^{-/-}$ animals diabetic for 2 months showed no inhibition or exacerbation of leukocyte-mediated endothelial death (FIG. 8). Acute (1 h) incubation of leukocytes ex vivo with Ret-NH$_2$ did not significantly reduce the diabetes-induced cytotoxicity of leukocytes toward endothelial cells (leukocytes from WT diabetic controls killed 193%±32 of cells killed by nondiabetic controls vs. 172±17 for leukocytes from WT diabetics treated for 1 hour with Ret-NH$_2$). Thus, inhibition of diabetes induced abnormalities in leukocytes by Ret-NH$_2$ in vivo apparently is not due to a direct effect on the leukocytes or endothelial cells per se, and thus is more likely mediated indirectly where Ret-NH$_2$ is stored under the influence of LRAT.

Figure 9:
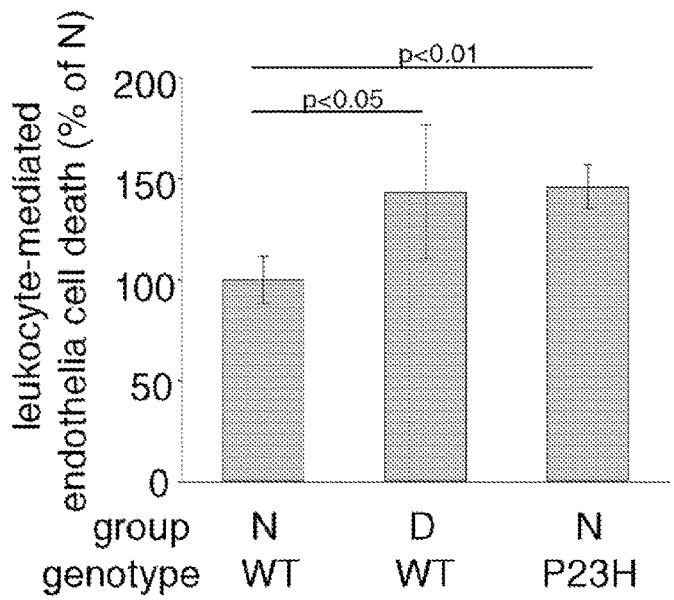
FIG. 9 illustrates a graph showing experimental damage to retinal photoreceptors by the P23H mutation of rhodopsin causes circulating leukocytes to become cytotoxic towards retinal endothelial cells. All animals were studied at 4 months of age. n=3-4 in all groups.

We postulated that disrupted cellular metabolism or damage to the outer retina/RPE might activate circulating leukocytes thus contributing to their increased cytotoxicity and that such cytotoxicity could be inhibited by Ret-NH$_2$ administration. We tested the first part of this postulate by measuring leukocyte-mediated killing of retinal endothelial cells in non-diabetic animals having different kinds of localized retinal injury (slow retinal degeneration due to mutant photoreceptor rhodopsin (P23H mutation) or LRAT deficiency). As shown in FIGS. 8 and 9, deficiencies of LRAT in the RPE or a P23H mutation of rhodopsin in photoreceptor cells led to increased killing of retinal endothelial cells by circulating leukocytes. Thus, even dysfunction or damage to the outer retina that might not be clinically detectable could suffice to increase cytotoxicity of leukocytes against retinal endothelial cells under a variety of conditions. Mechanisms by which this localized injury to the outer retina causes activation of circulating leukocytes is not known.

The unique effects of Ret-NH$_2$ as reported herein offer novel mechanistic insight into the pathogenesis of DR. We postulate that slowing the visual cycle at RPE65 by Ret-NH$_2$ slows subsequent phototransduction and the demand on mitochondria, which then reduces superoxide generation and slows the rate of capillary degeneration. One mechanism for the capillary degeneration potentially involves leukocytes (FIG. 10). Another not mutually exclusive possibility is that alterations within the photoreceptor/RPE unit induce secondary changes in Muller cells or retinal microglia, which are known to develop oxidative stress and a pro-inflammatory state in diabetes, and which could interact with photoreceptor cells and other retinal neurons and the retinal vasculature.

Example 2

In this Example, we investigated the contribution of several GPCRs and their downstream signaling pathways to superoxide generation by retina and retinal cells. We focused initially on adrenergic receptors (ARs) and 5-hydroxytryptamine (serotonin) receptors (HTRs) because these receptors were identified in retinas from multiple species by transcriptome analysis, and HTR agonists were shown by others to inhibit retinal degenerative diseases. Although these receptors had not been previously implicated in diabetic retinopathy, our present findings demonstrate that pharmacologic manipulation of these receptors can regulate superoxide generation by retinas and retinal cells exposed to elevated glucose. Moreover, pharmacologic inhibition of either the α1-AR or downstream NADPH oxidase (both components of the Gq-regulated signaling pathway) lowered the diabetes-induced increase in retinal oxidative stress, expression of proinflammatory proteins by the retina, and the resulting degeneration of retinal capillaries. These results identify GPCRs and their downstream pathways as novel therapeutic targets that can reduce retinal superoxide generation and the histopathology of diabetic retinopathy.

Materials and Methods

Chemicals

Doxazosin (Dox), apocynin (Apo), U73122, 2-aminoethoxydiphenyl borate (2-APB), ruthenium red, guanabenz (Gub), and brimonidine (Brim) were obtained from Sigma Chemicals (St. Louis, Mo., USA). Lofexidine (Lof) was from Santa Cruz Biotechnology (Santa Cruz, Calif., USA). LY 215840, RO 04-6790, RS 23597-190, and SQ 22536 were purchased from TOCRIS Biosciences (Bristol, United Kingdom). Sp-5,6-dichloro-1-b-D-ribofuranosylbenzimidazole-39,59-monophosphorothioate, dibutyryl cAMP, isobutylmethylxanthine, 1-methyl-3-isobutylxanthine (IBMX), and KT5720 were obtained from Enzo Life Sciences (Farmingdale, N.Y., USA).

In Vitro Studies

For initial drug candidate screening, we used a well-studied transformed cell line (661W) of retinal cells. The identity of these cells was confirmed by the positive identification of cone opsin mRNA and other proteins previously identified in this cell line. These cells were passaged in DMEM medium containing 5 mM glucose and 10% fetal bovine serum. For experiments, the fetal serum was reduced to 2%, and cells were incubated in either 5 or 30 mM glucose for 4 days with media changed every other day. Test agents were added to the media at 2-3 concentrations, each based on published reports as summarized in Table 2, with DMSO used as a control. Test drug concentrations that best reduced superoxide generation are shown in the figures. Cells were harvested by adding a trypsin-EDTA solution (0.5% and 0.02%, w/v) to the culture followed by centrifugation. In some experiments, Dox and Gub or Dox and RO 04-6790 were concurrently administered at suboptimal doses for 4 days. Effects of optimal concentrations of these drugs (selected for their ability to inhibit superoxide generation in 30 mM glucose) on cell death after 4 days are shown in Supplemental Table S1.

TABLE 2

Agents affecting signaling pathways studied in vitro

| Doxazosin (Dox) | $\alpha_1$-AR antagonist | $G_q$ | 10, 100, 1000 |
|---|---|---|---|
| Phenoxybenzamine (PBA) | $\alpha$-AR antagonist | $G_q$ | 10, 20 |
| Prazosin (PRA) | $\alpha_1$-AR antagonist | $G_q$ | 0.5, 5 |
| U73122 | PLC inhibitor | — | 1, 5, 10 |
| 2-APB | $IP_3$ receptor inhibitor | — | 10, 100, 200 |
| Ruthenium red (RR) | Calcium release from ER inhibitor | — | 5, 10 |
| Apocynin (Apo) | NADPH oxidase inhibitor | — | 10, 100, 1000 |
| Lofexidine (Lof) | $\alpha_2$-AR agonist | $G_i$ | 10, 100, 1000 |
| Guanabenz (Gub) | $\alpha_2$-AR agonist | $G_i$ | 1, 10 |
| Brimonidine (Brim) | $\alpha_2$-AR agonist | $G_i$ | 1, 10 |
| LY 215840 (LY) | 5-$HT_2$R/5-$HT_7$R antagonist | $G_s$, $G_q$ | 10, 100 |
| RO 04-6790 (RO) | 5-$HT_6$R antagonist | $G_s$ | 10, 100 |
| RS 23597-190 (RS) | 5-$HT_4$R antagonist | $G_s$ | 10, 100 |
| Dibutyryl cAMP (db cAMP) | Adenylate cyclase agonist | $G_s$ | 200, 500, 1000 |
| sp-5,6-DCI-cBIMPS | cAMP analog, PKA activator | $G_s$ | 1, 10, 50 |
| SQ 22536 (SQ) | Adenylate cyclase antagonist | $G_s$ | 50, 500 |
| IBMX | Phosphodiesterase inhibitor | $G_s$ | 30, 100, 225 |
| KT5720 | PKA inhibitor | $G_s$ | 0.05, 2 |
| Forskolin | Adenylate cyclase agonist | $G_s$ | 10 |

Assays performed in vitro with 661W cells are described in the Materials and Methods section.

Retinal Explants

Eyes were enucleated from adult C57Bl/6J mice and immediately immersed in ice-cold DMEM containing 10% fetal bovine serum, penicillin (100 U/ml), and streptomycin (100 mg/ml). The posterior pole (including retina, retinal pigment epithelium, and sclera) was incubated for 4 days in DMEM in humidified incubators with 5% $CO_2$ at 37° C., thus keeping the retina in contact with the retinal pigmented epithelium. The culture medium was changed every other day. At the end of this incubation, the retina was separated from the retinal pigment epithelium prior to the assay for superoxide.

Animals

All experiments followed the guidelines set forth by the Association for Research in Vision and Ophthalmology Resolution on Treatment of Animals in Research and the Institutional Animal Care and Use Committee at Case Western Reserve University. Insulin-deficient diabetes was induced in 2-month-old fasted male C57Bl/6J mice by intraperitoneal injections of streptozotocin [55 mg/kg body weight (BW)] on 5 consecutive days. Insulin was given as needed (0-0.2 units every 2-3 days) to maintain BW while allowing chronic hyperglycemia, polyuria, and hyperphagia. Blood glucose and hemoglobin A1c (HbA1c) were measured as reported previously. All therapeutics were administered by intraperitoneal injection in DMSO. Diabetic and age-matched nondiabetic controls were studied after 2 durations of diabetes (2 and 8 months).

Drugs Administered In Vivo

Diabetic mice were treated with (i) the $\alpha_1$-AR antagonist, Dox (10 mg/kg BW, daily intraperitoneal injection in DMSO); (ii) the NADPH oxidase inhibitor, Apo (36 mg/kg BW; daily intraperitoneal injection in DMSO); (iii) the PLC inhibitor, U73122 (6.25 mg/kg BW; daily intraperitoneal injection in DMSO; or (iv) the calcium channel inhibitor, 2-APB (6.25 mg/kg BW; daily intraperitoneal injection in DMSO). The a2-AR agonist, Lof, also was given to animals (dose initially was 2 mg/kg BW daily via intraperitoneal injection in DMSO). Doses were selected based on prior publications or initial dosing studies (data not shown). In all the above experiments, DMSO was injected intraperitoneally as the vehicle control.

Superoxide Generation

Retinas or isolated cells were incubated in 200 ml of Krebs-[4-(2-hydroxyethyl)-1-piperazineethanesulfonic acid buffer, pH 7.2, with 5 or 25 mM glucose for 5 minutes at 37° C. in 5% $CO_2$. Luminescence indicating the presence of superoxide was measured 5 minutes after addition of 0.54 mM (final concentration) lucigenin, as published previously. Luminescence intensity is reported in arbitrary units per milligram protein. To confirm the results obtained by the lucigenin method, we also measured reactive oxygen species with a 29.79 dichlorofluoresce in acetate method previously reported by Best et al. Results obtained with this alternate method were consistent with those found with lucigenin (data not shown).

Intracellular cAMP Assay

Cells (661W) were incubated with either 5 mM glucose, 30 mM glucose, or 30 mM glucose containing drugs at their indicated concentrations for 4 days. Intracellular cAMP levels were measured with the cAMP Biotrak Enzyme Immunoassay System (GE Healthcare Life Sciences, Piscataway, N.J., USA). To ensure equal protein concentrations, cell numbers in each sample were determined, and the volume of lysis buffer was adjusted accordingly. Isobutylmethylxanthine (1 mM) was included in the lysis buffer to inhibit cAMP-dependent phosphodiesterase activity.

Immunoblots

Retinal homogenates were separated by SDS-PAGE and incubated with either anti-rat intercellular adhesion molecule-1 (1:2000 dilution; R&D Systems, Minneapolis, Minn., USA) or the anti inducible isoform of nitric oxide synthase (iNOS; 1:1000 dilution; Santa Cruz Biotechnology, Santa Cruz, Calif., USA). Protein levels were quantified relative to β-actin loading controls (1:3000 dilution; Abcam, Cambridge, Mass., USA) in the same samples.

RT-PCR

To confirm that 661W cells were from photoreceptor cells, we used PCR for red/green opsin. Methods and results are summarized in the Supplemental Material.

Permeability

Retinal permeability was measured in eyes from animals that were diabetic for 8 months and their age-matched controls by using a fluorescently labeled tracer as described previously. Briefly, sterile FITC-bovine serum albumin (BSA; 50 mg/ml) in PBS (NaCl, 0.138 M; KCl, 0.0027 M; pH 7.4) was injected into the tail vein of mice at 100 mg/g BW. The dye circulated for 20 minutes before blood samples were collected and eyes were enucleated. Eyes were fixed in ice cold 4% paraformaldehyde, infused with sucrose, and then frozen in optimal cutting temperature compound in isopentane on dry ice. Retinal cryosections were imaged by fluorescence microscopy. Two images per eye were obtained on either side of the optic disc in the inner plexiform layer, and 2 sections per eye were imaged to generate an average image pixel density in the neural retina exclusive of any vessels. Relative average value fluorescence increases were normalized to the relative plasma fluorescence for final determinations of retinal dye accumulation. Because diabetes can increase glycation and other processes that cause autofluorescence and thus might confound interpretation of fluorescence data after injection of FITC-BSA, preliminary studies of retinal sections after long-term diabetes were carried out to evaluate possible autofluorescence. Our methods failed to detect an increase in autofluorescence (fluorescence in the FITC channel in the absence of FITC-BSA) caused by diabetes, so no correction of the permeability data was made.

Diabetes-Induced Retinal Histopathology

After 8 months of diabetes, 1 retina from each mouse was isolated for assessment of capillary histopathology, as described previously. Briefly, formalin-fixed retina was digested with 40 U/mL elastase (Calbiochem, San Diego, Calif., USA) for 2-3 hours. When totally freed of neural cells, the isolated retinal vasculature was laid out on a glass microscope slide, dried, and stained with hematoxylin and periodic acid-Schiff. Degenerated (acellular) capillaries were quantified in a masked manner in 6-7 field areas corresponding to the midretina. To evaluate possible photoreceptor degeneration in the long-term studies, the other eye was sectioned, and the number of cells in the outer nuclear layer from 2 areas on either side of the optic nerve (~300 µm from the optic nerve) was counted, and the 4 resulting values were averaged together to compute a single estimate for each animal.

Visual Function

Spatial frequency threshold and contrast sensitivity were measured after 2 and 8 months of diabetes as previously described, except that at 2 months, only a single spatial frequency (0.064 c/d) was measured. The grader was masked with respect to the animals' experimental group. Although nondiabetic mice could be differentiated from diabetic animals based on BW, investigators could not discern group identity because some diabetics were treated with agents, whereas others were not.

Statistical Analyses

Data are expressed as means±SD except for the permeability and contrast sensitivity studies, where data are expressed as means±SEM. All statistical analyses were performed with ANOVA, followed by Fisher's test, except for the full contrast sensitivity curve. The latter was analyzed by repeated-measures ANOVA to account for the testing of each animal at multiple spatial frequencies. Values of $P<0.05$ were considered statistically significant.

Results

In Vitro Studies

Figure 11:
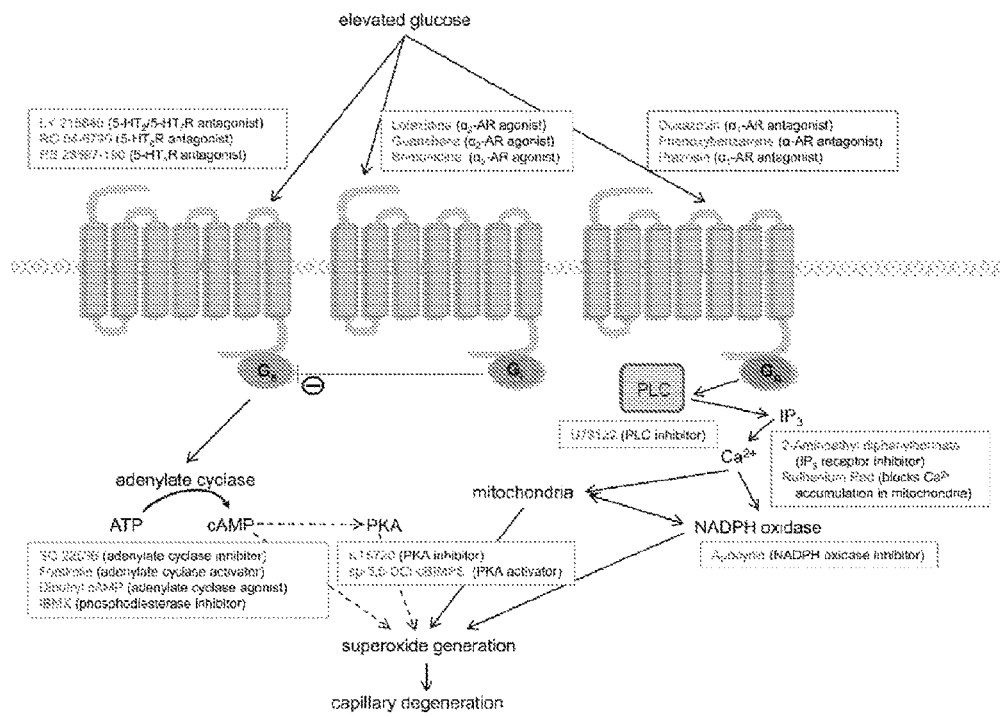
FIG. 11 illustrates a schematic showing relationships of major GPCR signaling pathways (Gs, Gi, and Gq) to superoxide generation and drugs used in vitro to test these relationships.

In vitro studies were done to evaluate the contribution of $G_s$-, $G_i$-, and $G_q$-mediated GPCR signaling pathways to the increase in superoxide generation by 661W cells incubated in diabetes-like (30 mM) concentrations of glucose. The identities of agonists and antagonists of AR and 5-HT pathways used for these studies are summarized in FIG. 11 and Table 2. Selection of this cell line for the in vitro studies was solely because it is a well-studied cell line derived from retinal cells; results from these studies do not specifically implicate cones in the pathology of diabetic retinopathy.

$G_q$-mediated signaling is known to activate NADPH oxidase, making this signaling pathway of special interest as a potential contributor to the generation of superoxide during elevated glucose concentrations and diabetes. Pharmacologic inhibition of the $\alpha_1$-AR with either Dox, PBA, or PRA (FIG. 12) significantly inhibited glucose-induced generation of superoxide by 661W cells. Because the $\alpha_1$-AR is known to regulate the activity of NADPH oxidase via activation of PLC, generation of inositol triphosphate ($IP_3$), and calcium release from the endoplasmic reticulum (ER), we pharmacologically inhibited each of these steps in vitro (FIG. 12).

Figure 13:
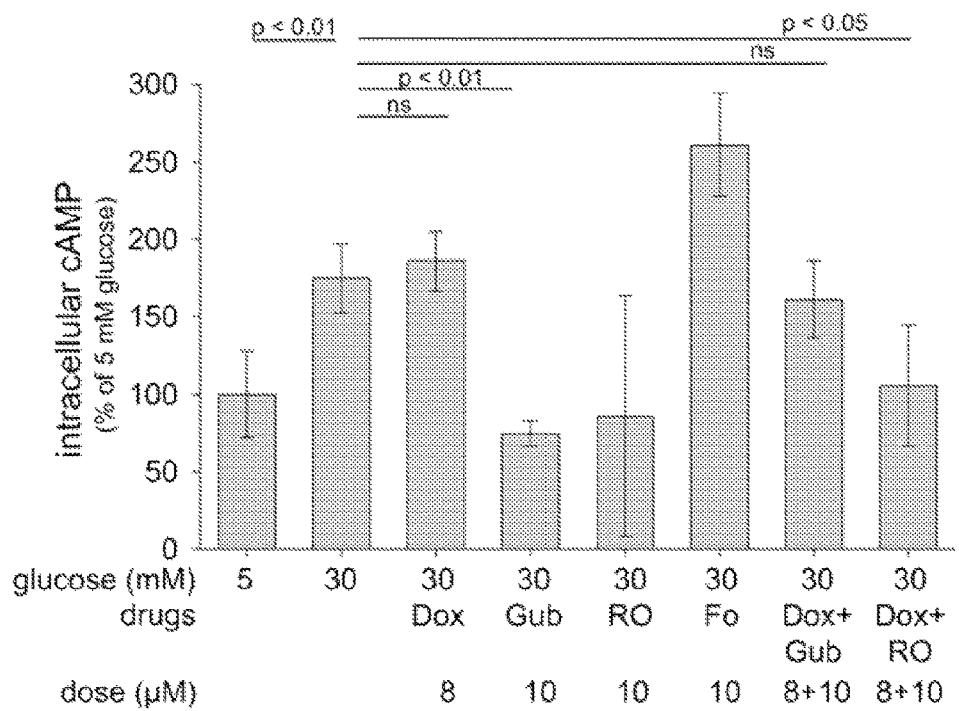
FIG. 13 illustrates a graph showing the effects of inhibitors of $\alpha_1$-ARs or serotonin receptors (5-HTRs), or activators of a2-ARs on cAMP levels in 661W cells. Studies were performed as described in the legend for FIG. 2. In some cases, drugs were combined for the full 4 days of study. Fo (forskolin) activates adenylyl cyclase and thus increases intracellular levels of cAMP. RO (RO 04-6790) is a 5-HT6R antagonist. n=3 for all groups, except n=2 for RO and Fo groups.

Pharmacologic inhibition of PLC by U73122, $IP_3$ receptors with 2-APB, calcium release from the ER by ruthenium red, or NADPH oxidase with Apo also significantly inhibited the glucose-induced increase in superoxide generation by these cells. α1-AR signaling has not been found to affect cAMP, and consistent with this observation, Dox did not inhibit the glucose-induced increase in cAMP (FIG. 13).

Activation of the $G_s$ pathway leads to accumulation of cAMP. In addition to β-ARs, several 5-HTRs, including 5-HT$_4$R and 5-HT$_7$R, are known to signal via the $G_s$ pathway. The cAMP mimic, dibutyryl cAMP, and the phosphodiesterase inhibitor, IBMX, both increased the generation of superoxide in vitro. Inhibition of signaling with the 5-HT$_2$/5-HT$_7$R antagonist, LY215840, or antagonists of the 5-HT$_6$R (RO 04-6790) or 5-HT$_4$R (RS 23597-190) significantly inhibited superoxide production by 661W cells in high glucose, as did the adenylate cyclase inhibitor, SQ 22536. The most effective doses tested in vitro are summarized in FIG. 14. These results demonstrate that elevating cAMP levels increased the production of superoxide in hyperglycemia in a retinal cell culture system. Because the effects of cAMP accumulation are often mediated via cAMPdependent protein kinase (PKA), we tested the effect of PKA inhibition by KT5720 on superoxide generation. Here we found that PKA inhibition did not decrease superoxide production, but instead significantly increased it (FIG. 14), suggesting that superoxide generation by retinal cells in high glucose does not require PKA signaling.

Activation of Gi-mediated signaling is known to inhibit adenylate cyclase. Consistent with this observation, activation of α-AR signaling by Gub significantly inhibited cAMP generation in high glucose (FIG. 13). Thus, we tested whether stimulation of α2-AR signaling would also inhibit superoxide generation in high glucose. As shown in FIG. 5, several agonists of the α2-AR (Lof, Gub, and Brim) did indeed significantly inhibit superoxide generation by 661W cells in 30 mM glucose.

To further investigate the impact of G-coupled signaling pathways on superoxide generation by retinal cells in high glucose, we tested whether suboptimal doses of therapeutics that affected different G protein signaling pathways would have additive effects on superoxide inhibition (FIG. 16). Simultaneous inhibition of 5-HTRs (that signal through the Gs pathway) and $\alpha_1$-AR ($G_q$ pathway) with suboptimal doses of Dox and RO 04-6790 caused significantly greater inhibition of superoxide generation than either drug alone (FIG. 16). Simultaneous activation of the $G_i$- and inhibition of $G_q$-mediated signaling pathways with suboptimal doses of Dox and Gub showed less than an additive inhibitory effect.

Retinal Explants

Incubation of retinal explants in 30 mM glucose for 4 days resulted in a significant increase in superoxide generation compared with their incubation in 5 mM glucose (FIG. 17). This increase was significantly inhibited by either Dox, Gub, or RO and was marginally increased by the PKA inhibitor, KT5720. These results were very consistent those obtained with 661W cells, again indicating that the cAMP driven increase in superoxide was not mediated via PKA.

In Vivo Studies

Based on our encouraging in vitro screening results, we proceeded to in vivo studies focusing initially on the $\alpha_1$- and $\alpha_2$-ARs known to be prevalent in the retina. Dox was used to inhibit the $\alpha_1$-ARs, and Lof was used as an agonist for the $\alpha_2$-ARs. Both compounds were administered daily for 2 months, starting promptly after the initiation of diabetes. Lof (initial daily dose of 2 mg/kg BW) was toxic to a number of diabetic animals, so was not studied further in vivo.

Diabetic mice from all experimental groups in the long-term experiment had levels of HbA1c and blood glucose that were significantly greater (P, 0.05) than levels found in age-matched nondiabetic controls. Average BWs and non-fasting glucose and HbA1c levels for the animal groups in the 8-month experiment are summarized in Table 3. Clinical data for diabetic groups studied for 2 months were similar. All mice appeared healthy and none had lost BW, although diabetic mice did not gain weight at a normal rate.

TABLE 3

Therapeutics not affecting metabolic control over an 8 month period of diabetes in mice

| Condition and treatment | n | Final BW (g) | Blood glucose (nonfasting; mg/dl) | HbA1c (%) |
|---|---|---|---|---|
| Non-diabetic control | 8 | 46 6 3 | 153 6 25 | 3.3 6 0.2 |
| Diabetic (8 mo) | 8 | 29 6 2 | 519 6 34 | 11.1 6 0.6 |
| Diabetic (8 mo) Dox | 8 | 28 6 2 | 483 6 69 | 10.8 6 1.2 |
| Diabetic (8 mo) Apo | 8 | 26 6 3 | 487 6 68 | 11.1 6 0.5 |

Except for final BW, clinical parameters were measured over the 8 month duration of diabetes as described in the Materials and Methods section.

In the 2-month studies, administration of Dox significantly suppressed the diabetes-induced increase in retinal superoxide generation (FIG. 18). Similar to our in vitro studies, the signaling mechanism by which the $\alpha$1-AR initiated retinal superoxide generation in diabetes also was studied in vivo. As shown in FIG. 18, inhibition of $\alpha_1$-ARs, PLC, IP3 receptors, or NADPH oxidase each significantly reduced superoxide generation by retinas from diabetic mice.

Figure 20:
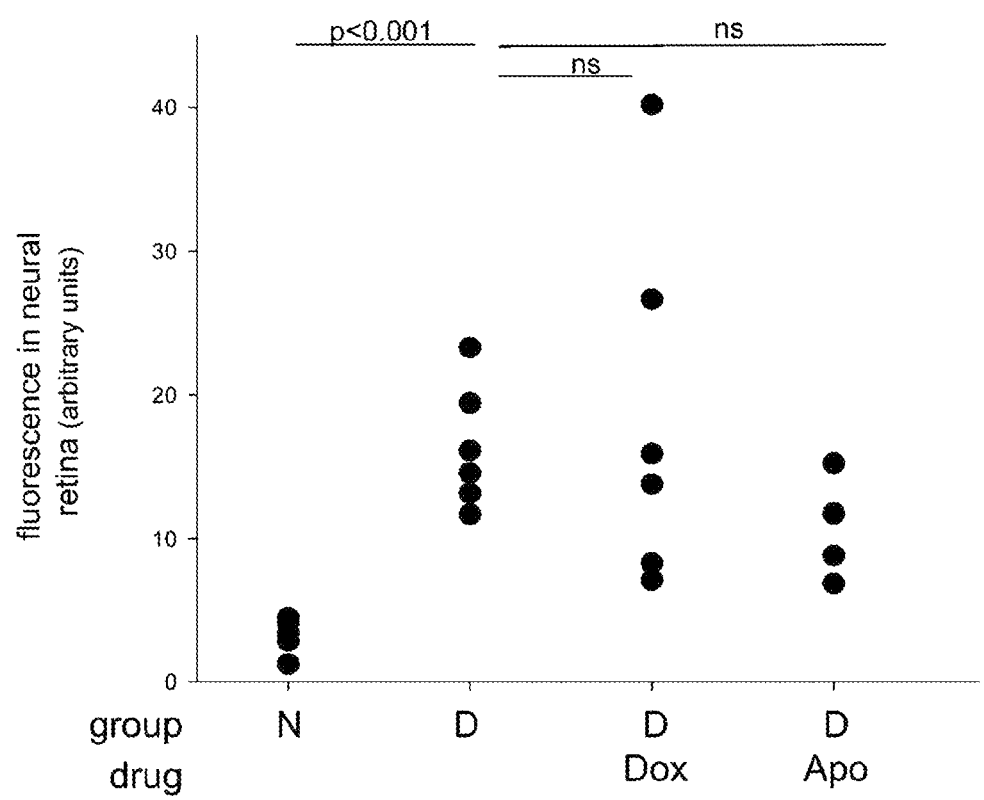
FIG. 20 illustrates a graph showing diabetes of 8 months duration significantly increased accumulation of FITC-BSA in the inner plexiform layer of mouse retina. FITC-albumin was injected intravenously and allowed to circulate for 20 minutes, and then fluorescence in areas of the inner plexiform layer was quantitated from retinal cross sections. Neither compound achieved a statistically significant difference from the control at 8 months of diabetes. n=4-6.

To determine whether $G_q$-mediated signaling pathways are involved in the long-term vascular pathology of diabetic retinopathy, we administered Dox or Apo to diabetic mice daily for 8 months. As expected, diabetes caused a significant increase in the number of degenerated retinal capillaries, leakage of FITC-BSA in the neural retina, and a significant impairment of visual function compared with age-matched nondiabetic controls (FIGS. 19 and 20). The number of degenerated capillaries was significantly reduced in diabetic mice treated with either Dox or Apo, as was the retinal generation of superoxide and expression of proinflammatory proteins (FIG. 19A, B). These studies clearly implicate the $\alpha_1$-AR signaling pathway in the oxidative stress affecting mouse retina in diabetes and show that Dox and Apo are valid pharmacologic agents capable of suppressing diabetic vascular degeneration. In contrast to the beneficial effect of both Dox and Apo on diabetes induced degeneration of retinal capillaries recorded at 8 months, neither therapy had a significant beneficial effect on the accumulation of FITC-albumin into the neural retina (a parameter of vascular leakage) (FIG. 10). Dox had a statistically significant effect on contrast sensitivity, but neither Dox nor Apo showed a beneficial effect on the spatial frequency threshold or maintained contrast sensitivity at normal levels (FIG. 19; Table 4). Neither diabetes of 8 months duration nor any tested therapeutic produced a loss of photoreceptor cells (Table 5), and diabetic controls actually had more photoreceptors than did age matched normal mice.

TABLE 4

Effect of Dox or Apo on diabetes-induced defects in the visual function of mice after 2 or 8 months duration of diabetes

| Category | Duration (mo) | n | Spatial frequency threshold (c/d) | Contrast sensitivity |
|---|---|---|---|---|
| Nondiabetic control | 2 | 4 | 0.399 ± 0.009 | 26.9 6 0.9$^a$ |
| Diabetic control | 2 | 4 | 0.379 ± 0.003b | 21.8 6 1.3$^{a,b}$ |
| Diabetic + Dox | 2 | 4 | 0.375 ± 0.008b | 23.1 6 0.8$^{a,b}$ |
| Diabetic + Apo | 2 | 4 | 0.374 ± 0.006b | 23.3 6 1.0$^{a,b}$ |
| Nondiabetic Diabetic control | 8 | 5 | 0.396 ± 0.006 | FIG. 9D FIG. 9D |
| Diabetic + Dox Diabetic + Apo | 8 | 5 | 0.349 ± 0.006b | FIG. 9D FIG. 9D |

Assays were performed in vivo as described in the Materials and Methods section. All animals were 2 months of age at initiation of diabetes. At 0.064 c/d. bP, 0.01 compared with nondiabetic control.

TABLE 5

Diabetes of 8 months duration did not cause loss of retinal photoreceptor cells in C57B1/6J mice

| Category | Duration (mo) | n | Number of cell layers in outer nuclear layer |
|---|---|---|---|
| Nondiabetic control | 8 | 7 | 11.2 6 0.7 |
| Diabetic control | 8 | 6 | 12.6 6 0.8a |
| Diabetic + Dox | 8 | 7 | 11.6 6 0.3 |
| Diabetic + Apo | 8 | 7 | 11.9 6 0.4 | aP, 0.05 compared with nondiabetic control.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, we claim:

1. A method of treating diabetic retinopathy in a subject in need thereof, the method comprising:
    administering to the subject a therapeutically effective amount of one or more agent that inhibits and/or antagonizes the Gq signaling cascade in a retina cell, agent that inhibits or antagonizes the Gs signaling cascade in a retina cell or agent that activates Gi signaling in a retina cell to inhibit diabetes-induced superoxide generation and capillary degeneration.

2. The method of claim 1, comprising administering to the subject a therapeutically effective amount at least two of an agent that inhibits and/or antagonizes the Gq signaling cascade in a retina cell, an agent that inhibits or antagonizes the Gs signaling cascade in a retina cell or an agent that activates Gi signaling cascade in a retina cell.

3. The method of claim 2, comprising administering to the subject a therapeutically effective amount at least three of an agent that inhibits and/or antagonizes the Gq signaling cascade in a retina cell, an agent that inhibits or antagonizes the Gs signaling cascade in a retina cell and an agent that activates Gi signaling cascade in a retina cell.

4. The method of claim 1, the agent comprising at least one of an alpha 1 adrenergic receptor ($\alpha_1$-AR) antagonist, a PLC inhibitor, an IP$_3$ receptor inhibitor, an inhibitor Ca+ accumulation in mitochondria, a NADPH oxidase inhibitor, a 5-HT$_{2a}$ receptor antagonist, a 5-HT$_{2b}$ receptor antagonist, a 5-HT$_{2c}$ receptor antagonist, a 5-HT$_{2a/c}$ receptor antagonist, a 5-HT$_4$ receptor antagonist, a 5-HT$_6$ receptor antagonist, 5-HT$_7$ receptor antagonist, andenylyl cyclase inhibitor, an M3 receptor antagonist, an alpha-2 adrenergic receptor agonists, or a PKA activator.

5. The method of claim 1, the agent comprising one or more alpha 1 adrenergic receptor antagonists.

6. The method of claim 5, the alpha 1 adrenergic receptor antagonists comprising at least one of doxazosin, prazosin, tamsulosin, terazosin, phenxoxybenzamine, and 5-methylurapadil.

7. The method of claim 1, the agent comprising one or more serotonin receptor antagonists selected from the group consisting of a 5-HT$_{2a}$ receptor antagonist, a 5-HT$_{2b}$ receptor antogonist, a 5-HT$_{2c}$ receptor antagonist, a 5-HT$_{2a/c}$ receptor antagonist, a 5-HT$_4$ receptor antagonist, a 5-HT$_6$ receptor antagonist, and a 5-HT$_7$ receptor antagonist.

8. The method of claim 7, the serotonin receptor antagonist being selected from the group consisting of agomelatine, pizotifen, RS 23579-190, Ro 04-6790 (4-Amino-N-[2,6-bis(methylamino)-4-pyrimidinyl]benzenesulfonamidev), SGS 518 oxalate (1-methyl-3-(1-methyl-4-piperidyl)indol-5-yl] 2,6-difluorobenzenesulfonate; oxalic acid), SB 269970 (3-({(2R)-2-[2-(4-Methyl-1-piperidinyl)ethyl]-1-pyrrolidinyl}sulfonyl)phenol hydrochloride (1:1)), LY 215840 ((8β)-N-[(1S,2R)-2-Hydroxycyclopentyl]-1-isopropyl-6-methylergoline-8-carboxamide), citalopram, escitalopram, fluoxetine, sertraline, paroxetine, fluvoxamine, venlafaxine, duloxetine, dapoxetine, nefazodone, imipramine, femoxetine, clomipramine, combinations thereof, and pharmaceutically acceptable salts thereof.

9. The method of claim 1, the agent comprising an adenylyl cyclase inhibitor.

10. The method of claim 9, the adenylyl cyclase inhibitor comprising 9-tetrahydrofuryl adenine, 2',5'-dideoxyadenosine, or 9-(cyclopentyl)-adenine.

11. The method of claim 1, the agent comprising a phospholipase C (PLC) inhibitor.

12. The method of claim 1, agent being delivered to the subject by at least one of topical administration, systemic administration, intravitreal injection, and intraocular delivery.

13. The method of claim 1, the agent being provided in an ocular preparation for sustained delivery.

14. The method of claim 1, further comprising administering retinylamine, retinylamine derivates, or a primary amine compound selected from the group consisting of:

3-Aminomethyl-5-methylhexanoic acid; 3-Aminomethyl-5-methylheptanoic acid; 3-Aminomethyl-5-methyl-octanoic acid; 3-Aminomethyl-5-methyl-nonanoic acid;
3-Aminomethyl-5-methyl-decanoic acid; 3-Aminomethyl-5-methyl-undecanoic acid;
3-Aminomethyl-5-methyl-dodecanoic acid; 3-Aminomethyl-5-methyl-tridecanoic acid;
3-Aminomethyl-5-cyclopropyl-hexanoic acid; 3-Aminomethyl-5-cyclobutyl-hexanoic acid;
3-Aminomethyl-5-cyclopentyl-hexanoic acid; 3-Aminomethyl-5-cyclohexyl-hexanoic acid; 3-Aminomethyl-5-trifluoromethyl-hexanoic acid; 3-Aminomethyl-5-phenyl-hexanoic acid;
3-Aminomethyl-5-(2-chlorophenyl)-hexanoic acid; 3-Aminomethyl-5-(3-chlorophenyl)-hexanoic acid; 3-Aminomethyl-5-(4-chlorophenyl)-hexanoic acid; 3-Aminomethyl-5-(2-methoxyphenyl)-hexanoic acid; 3-Aminomethyl-5-(3-methoxyphenyl)-hexanoic acid; 3-Aminomethyl-5-(4-methoxyphenyl)-hexanoic acid; 3-Aminomethyl-5-(phenylmethyl)-hexanoic acid; (S)-3-(Aminomethyl)-5-methylhexanoic acid; (R)-3-(Aminomethyl)-5-methylhexanoic acid; (3R,4S)-3-Aminomethyl-4,5-dimethyl-hexanoic acid; 3-Aminomethyl-4,5-dimethyl-hexanoic acid; (3R,4S)-3-Aminomethyl-4,5-dimethyl-hexanoic acid MP; (3S,4S)-3-Aminomethyl-4,5-dimethyl-hexanoic acid; (3R,4R)-3-Aminomethyl-4,5-dimethyl-hexanoic acid MP; 3-Aminomethyl-4-isopropyl-hexanoic acid; 3-Aminomethyl-4-isopropyl-heptanoic acid; 3-Aminomethyl-4-isopropyl-octanoic acid; 3-Aminomethyl-4-isopropyl-nonanoic acid; 3-Aminomethyl-4-isopropyl-decanoic acid; 3-Aminomethyl-4-phenyl-5-methyl-hexanoic acid; (3S,5S)-3-Aminomethyl-5-methoxy-hexanoic acid; (3S,5S)-3-Aminomethyl-5-ethoxy-hexanoic acid; (3S,5S)-3-Aminomethyl-5-propoxy-hexanoic acid; (3S,5S)-3-Aminomethyl-5-isopropoxy-hexanoic acid; (3S,5S)-3-Aminomethyl-5-tert-butoxy-hexanoic acid; (3S,5S)-3-Aminomethyl-5-fluoromethoxy-hexanoic acid; (3S,5S)-3-Aminomethyl-5-(2-fluoro-ethoxy)-hexanoic acid; (3S,5S)-3-Aminomethyl-5-(3,3,3-trifluoro-propoxy)-hexanoic acid; (3S,5S)-3-Aminomethyl-5-phenoxy-hexanoic acid; (3S,5S)-3-Aminomethyl-5-(4-chloro-phenoxy)-hexanoic acid; (3S,5S)-3-Aminomethyl-5-(3-chloro-phenoxy)-hexanoic acid; (3S,5S)-3-Aminomethyl-5-(2-chloro-phenoxy)-hexanoic acid; (3S,5S)-3-Aminomethyl-5-(4-fluoro-phenoxy)-hexanoic acid; (3S,5S)-3-Aminomethyl-5-(3-fluoro-phenoxy)-hexanoic acid; (3S,5S)-3-Aminomethyl-5-(2-fluoro-phenoxy)-hexanoic acid; (3S,5S)-3-Aminomethyl-5-(4-methoxy-phenoxy)-hexanoic acid; (3S,5S)-3-Aminomethyl-5-(3-methoxy-phenoxy)-hexanoic acid; (3S,5S)-3-Aminomethyl-5-(2-methoxy-phenoxy)-hexanoic acid; (3S,5S)-3-Aminomethyl-5-(4-nitro-phenoxy)-hexanoic acid; (3S,5S)-3-Aminomethyl-5-(3-nitro-phenoxy)-hexanoic acid; (3S,5S)-3-Aminomethyl-5-(2-nitro-phenoxy)-hexanoic acid; (3S,5S)-3-Aminomethyl-6-hydroxy-5-methyl-hexanoic acid; (3S,5S)-3-Aminomethyl-6-methoxy-5-methyl-hexanoic acid; (3S,5S)-3-Aminomethyl-6-ethoxy-5-methyl-hexanoic acid; (3S,5S)-3-Aminomethyl-5-methyl-6-propoxy-hexanoic acid; (3S,5S)-3-Aminomethyl-6-isopropoxy-5-methyl-hexanoic acid; (3S,5S)-3-Aminomethyl-6-tert-butoxy-5-methyl-hexanoic acid; (3S,5S)-3-Aminomethyl-6-fluoromethoxy-5-methyl-hexanoic acid; (3S,5S)-3-Aminomethyl-6-(2-fluoro-ethoxy)-5-methyl-hexanoic acid; (3S,5S)-3-Aminomethyl-5-methyl-6-(3,3,3-trifluoro-propoxy)-hexanoic acid; (3S,5S)-3-Aminomethyl-5-methyl-6-phenoxy-hexanoic acid; (3S,5S)-3-Aminomethyl-6-(4-chloro-phenoxy)-5-methyl-hexanoic acid; (3S,5S)-3-Aminomethyl-6-(3-chloro-phenoxy)-5-methyl-hexanoic acid; (3S,5S)-3-Aminomethyl-6-(2-chloro-phenoxy)-5-methyl-hexanoic acid; (3S,5S)-3-Aminomethyl-6-(4-fluoro-phenoxy)-5-methyl-hexanoic acid; (3S,5S)-3-Aminomethyl-6-(3-fluorophenoxy)-5-methyl-hexanoic acid; (3S,5S)-3-Aminomethyl-6-(2-fluoro-phenoxy)-5-methyl-hexanoic acid; (3S,5S)-3-Aminomethyl-6-(4-methoxy-phenoxy)-5-methyl-hexanoic acid; (3S,5S)-3-Aminomethyl-6-(3-methoxy-phenoxy)-5-methyl-hexanoic acid; (3S,5S)-3-Aminomethyl-6-(2-methoxy-phenoxy)-5-methyl-hexanoic acid; (3S,5S)-3-Aminomethyl-5-methyl 6-(4-trifluoromethyl-phenoxy)-hexanoic acid; (3S,5S)-3-Aminomethyl-5-methyl 6-(3-trifluoromethyl-phenoxy)-hexanoic acid; (3S,5S)-3-Aminomethyl-5-methyl 6-(2-trifluoromethyl-phenoxy)-hexanoic acid; (3S,5S)-3-Aminomethyl-5-methyl 6-(4-nitro-phenoxy)-hexanoic acid; (3S,5S)-3-Aminomethyl-5-methyl 6-(3-nitro-phenoxy)-hexanoic acid; (3S,5S)-3-Aminomethyl-5-methyl 6-(2-nitro-phenoxy)-hexanoic acid; (3S,5S)-3-Aminomethyl-6-benzyloxy-5-methyl-hexanoic acid; (3S,5S)-3-Aminomethyl-7-hydroxy-5-methyl-heptanoic acid; (3S,5S)-3-Aminomethyl-7-methoxy-5-methyl-heptanoic acid; (3S,5S)-3-Aminomethyl-7-ethoxy-5-methyl-heptanoic acid; (3S,5S)-3-Aminomethyl-5-methyl-7-propoxy-heptanoic acid; (3S,5S)-3-Aminomethyl-7-isopropoxy-5-methyl-heptanoic acid; (3S,5S)-3-Aminomethyl-7-tert-butoxy-5-methyl-heptanoic acid; (3S,5S)-3-Aminomethyl-7-fluoromethoxy-5-methyl-heptanoic acid; (3S,5S)-3-Aminomethyl-7-(2-fluoro-ethoxy)-5-methyl-heptanoic acid; (3S,5S)-3-Aminomethyl-5-methyl-7-(3,3,3-trifluoro-propoxy)-heptanoi-c acid; (3S,5S)-3-Aminomethyl-7-benzyloxy-5-methyl-heptanoic acid; (3S,5S)-3-Aminomethyl-5-methyl-7-phenoxy-heptanoic acid; (3S,5S)-3-Aminomethyl-7-(4-chloro-phenoxy)-5-methyl-heptanoic acid; (3S,5S)-3-Aminomethyl-7-(3-chloro-phenoxy)-5-methyl-heptanoic acid; (3S,5S)-3-Aminomethyl-7-(2-chloro-phenoxy)-5-methyl-heptanoic acid; (3S,5S)-3-Aminomethyl-7-(4-fluoro-phenoxy)-5-methyl-heptanoic acid; (3S,5S)-3-Aminomethyl-7-(3-fluoro-phenoxy)-5-methyl-heptanoic acid; (3S,5S)-3-Aminomethyl-7-(2-fluoro-phenoxy)-5-methyl-heptanoic acid; (3S,5S)-3-Aminomethyl-7-(4-methoxy-phenoxy)-5-methyl-heptanoic acid; (3S,5S)-3-Aminomethyl-7-(3-methoxy-phenoxy)-5-methyl-heptanoic acid; (3S,5S)-3-Aminomethyl-7-(2-methoxy-phenoxy)-5-methyl-heptanoic acid; (3S,5S)-3-Aminomethyl-5-methyl-7-(4-trifluoromethyl-phenoxy)-heptan-oic acid; (3S,5S)-3-Aminomethyl-5-methyl-7-(3-trifluoromethyl-phenoxy)-heptan-oic acid; (3S,5S)-3-Aminomethyl-5-methyl-7-(2-trifluoromethyl-phenoxy)-heptan-oic acid; (3S,5S)-3-Aminomethyl-5-methyl-7-(4-nitro-phenoxy)-heptanoic acid; (3S,5S)-3-Aminomethyl-5-methyl-7-(3-nitro-phenoxy)-heptanoic acid; (3S,5S)-3-Aminomethyl-5-methyl-7-(2-nitro-phenoxy)-heptanoic acid; (3S,5S)-3-Aminomethyl-5-methyl-6-phenyl-hexanoic acid; (3S,5S)-3-Aminomethyl-6-(4-chloro-phenyl)-5-methyl-hexanoic acid; (3S,5S)-3-Aminomethyl-6-(3-chloro-phenyl)-5-methyl-hexanoic acid; (3S,5S)-3-Aminomethyl-6-(2-chloro-phenyl)-5-methyl-hexanoic acid; (3S,5S)-3-Aminomethyl-6-(4-methoxy-phenyl)-5-methyl-hexanoic acid; (3S,5S)-3-Aminomethyl-6-(3-methoxy-phenyl)-5-methyl-hexanoic acid; (3S,5S)-3-Aminomethyl-6-(2-methoxy-phenyl)-5-methyl-hexanoic acid; (3S,5S)-3-Aminomethyl-6-(4-fluoro-phenyl)-5-methyl-hexanoic acid; (3S,5S)-3-Aminomethyl-6-(3-fluoro-phenyl)-5-methyl-hexanoic acid; (3S,5S)-3-Aminomethyl-6-(2-fluoro-phenyl)-5-methyl-hexanoic acid; (3S,5R)-3-Aminomethyl-5-methyl-7-phenyl-heptanoic acid; (3S,5R)-3-Aminomethyl-7-(4-chloro-phenyl)-5-methyl-heptanoic acid; (3S,5R)-3-Aminomethyl-7-(3-chloro-phenyl)-5-methyl-heptanoic acid; (3S,5R)-3-Aminomethyl-7-(2-chloro-phenyl)-5-methyl-heptanoic acid; (3S,5R)-3-Aminomethyl-7-(4-methoxy-phenyl)-5-methyl-heptanoic acid; (3S,5R)-3-Aminomethyl-7-(3-methoxy-phenyl)-5-methyl-heptanoic acid; (3S,5R)-3-Aminomethyl-7-(2-methoxy-phenyl)-5-methyl-heptanoic acid; (3S,5R)-3-Aminomethyl-7-(4-fluoro-phenyl)-5-methyl-heptanoic acid; (3S,5R)-3-Aminomethyl-7-(3-fluoro-phenyl)-5-methyl-heptanoic acid; (3S,5R)-3-Aminomethyl-7-(2-fluoro-phenyl)-5-methyl-heptanoic acid; (3S,5R)-3-Aminomethyl-5-methyl-oct-7-enoic acid; (3S,5R)-3-Aminomethyl-5-methyl-non-8-enoic acid; (E)-(3S,5S)-3-Aminomethyl-5-methyl-oct-6-enoic acid; (Z)-(3S,5S)-3-Aminomethyl-5-methyl-oct-6-enoic acid; (Z)-(3S,5S)-3-Aminomethyl-5-methyl-non-6-enoic acid; (E)-(3S,5S)-3-Aminomethyl-5-methyl-non-6-enoic acid; (E)-(3S,5R)-3-Aminomethyl-5-methyl-non-7-enoic acid; (Z)-(3S,5R)-3-Aminomethyl-5-methyl-non-7-enoic acid; (Z)-(3S,5R)-3-Aminomethyl-5-methyl-dec-7-enoic acid; (E)-(3S,5R)-3-Aminomethyl-5-methyl-undec-7-enoic acid; (3S,5S)-3-Aminomethyl-5,6,6-trimethyl-heptanoic acid; (3S,5S)-3-Aminomethyl-5,6-dimethyl-heptanoic acid; (3S,5S)-3-Aminomethyl-5-cyclopropyl-hexanoic acid; (3S,5S)-3-Aminomethyl-5-cyclobutyl-hexanoic acid; (3S,5S)-3-Aminomethyl-5-cyclopentyl-hexanoic acid; (3S,5S)-3-Aminomethyl-5-cyclohexyl-hexanoic acid; (3S,5R)-3-Aminomethyl-5-methyl-heptanoic acid; (3S,5R)-3-Aminomethyl-5-methyl-octanoic acid; (3S,5R)-3-Aminomethyl-5-methyl-nonanoic acid; (3S,5R)-3-Aminomethyl-5-methyl-decanoic acid; (3S,5R)-3-Aminomethyl-5-methyl-undecanoic acid; (3S,5R)-3-Aminomethyl-5-methyl-dodecanoic acid; (3S,5R)-3-Aminomethyl-5,9-dimethyl-decanoic acid; (3S,5R)-3-Aminomethyl-5,7-dimethyl-octanoic acid; (3S,5R)-3-Aminomethyl-5,8-dimethyl-nonanoic acid; (3S,5R)-3-Aminomethyl-6-cyclopropyl-5-methyl-hexanoic acid; (3S,5R)-3-Aminomethyl-6-cyclobutyl-5-methyl-hexanoic acid; (3S,5R)-3-Aminomethyl-6-cyclopentyl-5-methyl-hexanoic acid; (3S,5R)-3-Aminomethyl-6-cyclohexyl-5-methyl-hexanoic acid; (3S,5R)-3-Aminomethyl-7-cyclopropyl-5-methyl-heptanoic acid; (3S,5R)-3-Aminomethyl-7-cyclobutyl-5-methyl-heptanoic acid; (3S,5R)-3-Aminomethyl-7-cyclopentyl-5-methyl-heptanoic acid; (3S,5R)-3-Aminomethyl-7-cyclohexyl-5-methyl-heptanoic acid; (3S,5R)-3-Aminomethyl-8-cyclopropyl-5-methyl-octanoic acid; (3S,5R)-3-Aminomethyl-8-cyclobutyl-5-methyl-octanoic acid; (3S,5R)-3-Aminomethyl-8-cyclopentyl-5-methyl-octanoic acid; (3S,5R)-3-Aminomethyl-8-cyclohexyl-5-methyl-octanoic acid; (3S,5S)-3-Aminomethyl-6-fluoro-5-methyl-hexanoic acid; (3S,5S)-3-Aminomethyl-7-fluoro-5-methyl-heptanoic acid; (3S,5R)-3-Aminomethyl-8-fluoro-5-methyl-octanoic acid; (3S,5R)-3-Aminomethyl-9-fluoro-5-methyl-nonanoic acid; (3S,5S)-3-Aminomethyl-7,7,7-trifluoro-5-methyl-heptanoic acid; (3S,5R)-3-Aminomethyl-8,8,8-trifluoro-5-methyl-octanoic acid; (3S,5R)-3-Aminomethyl-5-methyl-8-phenyl-octanoic acid; (3S,5S)-3-Aminomethyl-5-methyl-6-phenyl-hexanoic acid; (3S,5R)-3-Aminomethyl-5-methyl-7-phenyl-heptanoic acid; and pharmaceutically acceptable salts thereof.

* * * * *